US007309696B2

(12) United States Patent
Kucera et al.

(10) Patent No.: US 7,309,696 B2
(45) Date of Patent: Dec. 18, 2007

(54) COMPOSITIONS AND METHODS FOR TARGETING CANCER CELLS

(75) Inventors: Louis S. Kucera, Pfafftown, NC (US); Ronald A. Fleming, Cary, NC (US); Khalid S. Ishaq, Chapel Hill, NC (US); Gregory L. Kucera, Winston-Salem, NC (US); Susan L. Morris-Natschke, Apex, NC (US)

(73) Assignees: Wake Forest University, Winston-Salem, NC (US); University of North Carolina at Chapel Hill, Chapel Hill, NC (US)

( * ) Notice: Subject to any disclaimer, the term of this patent is extended or adjusted under 35 U.S.C. 154(b) by 296 days.

(21) Appl. No.: 10/748,738

(22) Filed: Dec. 30, 2003

(65) Prior Publication Data

US 2004/0161398 A1    Aug. 19, 2004

Related U.S. Application Data

(62) Division of application No. 09/693,658, filed on Oct. 19, 2000, now Pat. No. 6,670,341.

(51) Int. Cl.
*A01N 43/04* (2006.01)
*A61K 31/70* (2006.01)
*C07H 19/00* (2006.01)
*C07H 19/048* (2006.01)

(52) U.S. Cl. ............................ 514/51; 514/43; 514/49; 514/50

(58) Field of Classification Search .................... None
See application file for complete search history.

(56) References Cited

U.S. PATENT DOCUMENTS

| | | | | |
|---|---|---|---|---|
| 2,086,585 | A | 7/1937 | Taub et al. | 260/127 |
| 2,087,132 | A | 7/1937 | Taub et al. | 260/127 |
| 2,108,765 | A | 2/1938 | Domagk | 167/30 |
| 2,209,383 | A | 7/1940 | Bock | 8/116 |
| 2,439,969 | A | 4/1948 | Fourneau | 260/338 |
| 2,445,393 | A | 7/1948 | Fourneau | 260/338 |
| 2,513,747 | A | 7/1950 | Sallman et al. | 260/338 |
| 2,606,909 | A | 8/1952 | Blicke | 260/338 |
| 2,689,790 | A | 9/1954 | Mowry et al. | 71/2.7 |
| 2,950,253 | A | 8/1960 | Kling et al. | 252/152 |
| 3,054,678 | A | 9/1962 | Michener et al. | 99/150 |
| 3,694,473 | A | 9/1972 | Eibl et al. | 260/403 |
| 4,093,714 | A | 6/1978 | Tolman et al. | 424/180 |
| 4,096,278 | A | 6/1978 | Queuille | 424/329 |
| 4,119,714 | A | 10/1978 | Kny et al. | 424/199 |
| 4,159,988 | A | 7/1979 | Eibl et al. | 260/340.9 R |
| 4,221,732 | A | 9/1980 | Oette et al. | 260/403 |
| 4,235,877 | A | 11/1980 | Fullerton | 424/89 |
| 4,291,024 | A | 9/1981 | Turcotte | 424/180 |
| 4,329,302 | A | 5/1982 | Hanahan et al. | 260/925 |
| 4,426,525 | A | 1/1984 | Hozumi et al. | 546/22 |
| 4,444,766 | A | 4/1984 | Bosies et al. | 424/211 |
| 4,471,113 | A | 9/1984 | MacCoss | 536/29 |
| 4,540,521 | A | 9/1985 | Garst et al. | 260/459 |
| 4,559,157 | A | 12/1985 | Smith et al. | 424/401 |
| 4,608,392 | A | 8/1986 | Jacquet et al. | 424/401 |
| 4,619,917 | A | 10/1986 | Lee et al. | 514/77 |
| 4,622,392 | A | 11/1986 | Hong et al. | 536/28.5 |
| 4,661,509 | A | 4/1987 | Gordon et al. | 514/397 |
| 4,724,232 | A | 2/1988 | Rideout et al. | 514/50 |
| 4,797,479 | A | 1/1989 | Shuto et al. | 536/28.5 |
| 4,816,450 | A | 3/1989 | Bell et al. | 514/25 |
| 4,820,508 | A | 4/1989 | Wortzman | 424/59 |
| 4,826,823 | A | 5/1989 | Cook et al. | 514/46 |

(Continued)

FOREIGN PATENT DOCUMENTS

DE    37 26 945 A1    2/1989

(Continued)

OTHER PUBLICATIONS

Aggarwal, S.K. et al., "Synthesis and Biological Evaluation of Prodrugs of Zidovudine," *J. Med. Chem.*, 33, 1505-10, 1990.

(Continued)

*Primary Examiner*—Patrick Lewis
(74) *Attorney, Agent, or Firm*—Morgan, Lewis & Bockius LLP

(57) ABSTRACT

The invention includes compositions and methods useful for treatment of a virus infection in a mammal by double-targeting the virus (i.e. targeting the virus at more than one stage of the virus life cycle) and thereby inhibiting virus replication. The compositions of the invention include compounds which comprise a phosphocholine moiety covalently conjugated with one or more antiviral agents (e.g. nucleoside analogue, protease inhibitor, etc.) to a lipid backbone. The invention also includes pharmaceutical compositions and kits for use in treatment of a virus infection in mammals. The methods of the invention comprise administering a compound of the invention, a pharmaceutically acceptable salt thereof, or a pharmaceutical composition of the invention, in an amount effective to treat the infection, to a mammal infected with a virus. Additionally, the invention includes compositions and methods useful for combating a cancer in a mammal and for facilitating delivery of a therapeutic agent to a mammalian cell. The compositions of the invention include compounds which comprise an alkyl lipid or phospholipid moiety covalently conjugated with an anticancer agent (e.g. a nucleoside analogue). The invention also includes pharmaceutical compositions and kits for combating a cancer and for facilitating delivery of a therapeutic agent to a mammalian cell. The methods of the invention comprise administering a compound of the invention, a pharmaceutically acceptable salt thereof, or a pharmaceutical composition of the invention, in an amount effective to combat a cancer or to facilitate delivery of a therapeutic agent to a mammalian cell.

45 Claims, 9 Drawing Sheets

U.S. PATENT DOCUMENTS

| | | | |
|---|---|---|---|
| 4,835,263 A | 5/1989 | Nguyen et al. | 536/27 |
| 4,837,023 A | 6/1989 | Eibl | 424/439 |
| 4,841,039 A | 6/1989 | Chu et al. | 536/29 |
| 4,880,782 A | 11/1989 | Eckstein et al. | 514/45 |
| 4,921,951 A | 5/1990 | Shuto et al. | 536/28.5 |
| 4,938,476 A | 7/1990 | Borch et al. | 514/476 |
| 4,992,478 A | 2/1991 | Geria | 514/782 |
| 4,997,761 A | 3/1991 | Jett-Tilton | 435/375 |
| 5,026,687 A | 6/1991 | Yarchoan et al. | 514/45 |
| 5,034,394 A | 7/1991 | Daluge | 514/261 |
| 5,138,045 A | 8/1992 | Cook et al. | 536/27 |
| 5,221,696 A | 6/1993 | Ke et al. | 514/786 |
| 5,496,546 A | 3/1996 | Wang et al. | 424/78.36 |
| 5,512,671 A | 4/1996 | Piantadosi | 536/26.1 |
| 5,614,548 A | 3/1997 | Piantadosi et al. | 514/440 |
| 5,633,388 A | 5/1997 | Diana et al. | 548/305.7 |
| 5,770,584 A | 6/1998 | Kucera et al. | 514/77 |
| 5,830,905 A | 11/1998 | Diana et al. | 514/322 |
| 5,846,964 A | 12/1998 | Ozeki | 514/182 |
| 5,891,874 A | 4/1999 | Colacino et al. | 514/234.5 |
| 5,922,757 A | 7/1999 | Chojkier | 514/458 |
| 5,962,437 A | 10/1999 | Kucera et al. | |
| 5,985,854 A | 11/1999 | Kozak | |
| 6,030,960 A | 2/2000 | Morris-Natschke et al. | 514/77 |
| 6,077,837 A | 6/2000 | Kozak | |
| 6,136,796 A | 10/2000 | Kozak | |
| 6,166,089 A | 12/2000 | Kozak | |
| 6,670,341 B1 | 12/2003 | Kucera et al. | 514/77 |

FOREIGN PATENT DOCUMENTS

| | | |
|---|---|---|
| DE | 39 34 820 A1 | 4/1991 |
| DE | 40 10 228 A1 | 10/1991 |
| DE | 199 14 474 | 10/1999 |
| EP | 0 094 586 | 11/1983 |
| EP | 0 109 255 | 5/1984 |
| EP | 0 142 333 | 5/1985 |
| EP | 0 145 303 | 6/1985 |
| EP | 0 146 258 | 6/1985 |
| EP | 0 252 310 | 1/1988 |
| EP | 0 310 109 | 4/1989 |
| EP | 0 335 396 | 4/1989 |
| EP | 0 348 859 | 1/1990 |
| EP | 0 350 287 | 1/1990 |
| EP | 0 416 401 | 3/1991 |
| EP | 0 434 450 | 6/1991 |
| EP | 0 506 704 | 7/1991 |
| EP | 0 632 048 | 1/1995 |
| FR | 1561630 | 3/1969 |
| GB | 2 239 243 A | 6/1991 |
| JP | 42-13841 | 8/1967 |
| JP | 49-100224 | 9/1974 |
| JP | 61-238793 | 10/1986 |
| JP | 1029312 | 1/1989 |
| JP | 08-268890 | 10/1996 |
| JP | 10-10591 | 4/1998 |
| WO | 90/00555 | 1/1990 |
| WO | 90/05736 | 5/1990 |
| WO | 90/15601 | 12/1990 |
| WO | 91/05558 | 5/1991 |
| WO | 91/09602 | 7/1991 |
| WO | 91/18914 | 12/1991 |
| WO | 91/19726 | 12/1991 |
| WO | 92/03462 | 3/1992 |
| WO | 92/06192 | 4/1992 |
| WO | 93/00910 | 1/1993 |
| WO | 93/08807 | 5/1993 |
| WO | 93/16091 | 8/1993 |
| WO | 93/16092 | 8/1993 |
| WO | 93/17020 | 9/1993 |
| WO | 93/21191 | 10/1993 |
| WO | WO 94/28908 | 12/1994 |
| WO | WO 96/06620 | 3/1996 |
| WO | WO 96/25147 * | 8/1996 |
| WO | WO 98/17679 | 4/1998 |
| WO | WO 98/22496 | 5/1998 |
| WO | WO 99/07734 | 2/1999 |
| WO | WO 01/19320 | 3/2001 |
| WO | WO 01/34614 | 5/2001 |

OTHER PUBLICATIONS

Alt M. et al., "Core Specific Antisense Phosphorthioate Oligodeoxynucleotides as Potent and Specific Inhibitors of Hepatitis C Viral Translation," *Archives of Virology* 142:589-599, 1997.

Alt M. et al., "Specific Inhibition of Hepatitis C Viral Gene Expression by Antisense Phosphorothioate Oligodeoxynucleotides," *Hepatology* 22:707-717, Sep. 1995.

Amari et al., "Isolation of Experimental Anti-AIDS Glycerophospholipids by Micro-Preparative Reversed-Phase High-Performance Liquid Chromatography," *Journal of Chromatography*, 590, 153-161, 1992.

Anderson, L. J. et al., "Antigenic Characterization of Respiratory Syncytial Virus Strains with Monoclonal Antibodies," *Journal of Infectious Diseases*, 151:626-633, Apr. 1985.

Attwood, M. R. et al., "The Design and Synthesis of Potent Inhibitors of Hepatitis C Virus NS3-4A Proteinase," *Antiviral Chemistry and Chemotherapy* 10:259-273, Sep. 1999.

Bartlett, *Infectious Diseases in Clinical Practice*, 5:172-179, 1996.

Berdel et al., "Cyto Toxicity of Thio Ether Lyso Phospho Lipids in Leukemias and Tumors of Human Origin," *Cancer Research*, vol. 43, 5538-5543, 1983.

Berenguer, M. et al., "Hepatitis C Virus in the Transplant Setting," *Antiviral Therapy* 3(Suppl. 3):125-136, 1998.

Boldanova, N. B. et al., "Protective Effect of Phosphatidylcholine-Containing Liposomes in Experimental Toxic Hepatitis," *Vopr. Med. Khim*, 32, No. 3 (1986) Chemical Abstracts 105, p. 67, Abstract No. 35587k (1986).

Bosies, E. et al., "Preparation of Lecithin Analogs as Retrovirucides and Virucides," *Chemical Abstracts*, 115CA; 72142p, 1991.

Braekman et al., *Proc. Amer. Soc. for Clinical Oncology*, Abstract # 810, 1997.

Capizzi, Investigational New Drugs 14: 249-256, 1996.

Chen, "Design and Synthesis of Novel Nucleoside Analogs as Potential Antiviral Agents," Abstract *American Assoc. of Pharmaceutical Scientists*, vol. 9, No. 10, 1992.

Chu M. et al., "Isolation and Structure of SCH 351633: A Novel Hepatitis C Virus (HCV) NS3 Protease Inhibitor from the Fungus *Penicillium griseofulvum,*" *Bioorganic and Medicinal Chemistry Letters* 9:1949-1952, 1999.

Chu M. et al., "Structure of Sch 68631: A New Hepatitis C Virus Proteinase Inhibitor from *Streptomyces* sp.," *Tetrahedron Letters* 37:7229-7232, 1996.

Coe et al., "Preparation of Nucleotide Mimics with Potent Inhibitor Activity Against HIV Reserve Transcriptase," *J. Chem. Soc.* Perkin Trans 1, 3378-3379, 1991.

Crumpton, S. et al., "Novel Lipid Analogs with Cytostatic and Cytocidal Activity," *Anticancer Research*, vol. 8, No. 6, pp. 1361-1366, Nov.-Dec. 1988.

Daniel, L. W. et al., "Alkyl-Linked Diglygerides Inhibit Protein Kinease C Activation by Diacylglycerols," *Biochemical & Biophysical Research Communications*, 151, 291-97, Feb. 29, 1988.

DeClerq, *Jounral of Medicinal Chemistry* 38: 2491-2517, 1995.

Del Pan et al., *Proc. Amer. Soc. for Clinical Oncology*, Abstract # 1384, 1997.

Dietzfelbinger, "Cytotoxic and Purging Effects of ET-18-OCH3 in Human Malignant Lymphoid Cell Lines in Vitro," Abstract 2472, *Proceedings of the American Assoc. for Cancer Res.*, 31, 416, Mar. 1990.

Domawchowske J. B. et al., "Respiratory Syncytial Virus Infection: Immune Response, Immunopathogenesis and Treatement," *Clinical Microbiology Reviews*, 12:298-309, Apr. 1999.

Englund, J. A., "Prevention Strategies for Respiratory Syncytial Virus: Passive and Active Immunization," *J. Pediatr.*, 135:38-44, Aug. 1999.
Eron et al., *AIDS* 12: F181-F189, 1998.
Falsey A. R. et al., "Acute Respiratory Tract Infection in Daycare Centers for Older Persons," *J Am Geriatric Soc.*, 43:30-36, 1995.
Falsey A. R. et al., "Viral Respiratory Infectious in the Institutionalized Elderly: Clinical and Epidemiologic Findings," *J Am Geriatric Soc.*, 40:115-119, 1992.
Fauci, *Nature (New Biology)*, 384: 529-534, 1996.
Fields, A. P. et al, "Human Immunodeficiency Virus Induces Phosphorylation of its Cell Surface Receptor," *Nature*, 333, 278-80, May 19, 1988.
Galderisi U. et al., "Antisense Oligonucleotides as Therapeutic Agents," *Journal of Cellular Physiology*, 181:251-257, 1999.
Gill et al., *Annals of Internal Medicine* 107: 502-505, 1987.
Glezen W. P. et al., "Risk of Primary Infection and Reinfection with Respiratory Syncytial Virus," *Am J Dis Child*, 140:543-546, 1986.
Goodman and Gilman, *The Pharmacological Basis of Therapeutics*, Ninth Ed., 1996.
Gordeev, K. et al., "Synthesis of Thio Analogs of Platlet Activating Factor (PAF)," *Abstract Bioorg. Khim.*, vol. 12, No. 7, pp. 951-955, 1986.
Graham, F. L. et al., "A New Technique for the Assay of Infectivity of Human Adenovirus 5-DNA," *Virology*, vol. 52, pp. 456-467, 1973.
Guerguerian, A. et al., "Ribavirin in Ventilated Respiratory Syncytial Virus Bronchiolitis: a Randomized, Placebo-Controlled Trial," *Am J Resp Crit Care Med.*, 160:829-834, 1999.
Hall C. B. et al., "Infectivity of Respiratory Syncytial Virus by Various Routes of Inoculation," *Infect Immun.*, 33:779-783, 1981.
Hall, C. B., "Nosocomial Respiratory Syncytial Virus Infections," *N Engl J Med.*, 293:1343-1346, 1975.
Hall C. B. et al., "Respiratory Syncytial Virus Infections Within Families," *N Engl J Med*, 294:414-419, 1976.
Hancock et al., "Analogs of Natural Lipids. VII. Synthesis of Cyclopentanoid Analogs of Phosphatidylcholine," *Journal of Lipid Research*, vol. 23, 183-189, 1982.
Harada, S. et al., "Infection of HTLV-III/LAV in HTLV-I-Carrying Cells MT-2 and MT-4 and Application in a Plaque Assay," *Science*, 229, 563-566, Aug. 9, 1985.
Hayashi et al., "Antitumor Activity of a Novel Nucleotide Derivative, 5'-(1,2 Dipalmitoyl-sn-glycero-3-phospho)-5-fluorouridine (TJ14026) on Murine Tumors," *Biol. Pharm. Bull.*, 16(8), 778-81, 1993.
Henderson, F.W. et al., "Respiratory-Syncytial-Virus Infections, Reinfections, and Immunity: a Prospective, Longitudinal Study in Young Children," *N Engl J Med,*, 300:530-534, 1979.
Hendrickson, H., et al., "A Facile Asymmetric Synthesis of Glycerol Phospholipid via Tritylglycidol Prepared by the Asymmetric Epoxidation of Allyl Alcohol," *Abstract Chem. Phys. Lipids*, vol. 53, No. 1, pp. 115-120, 1990.
Himmelmann, "Studies on the Cross Resistance Pattern of Membrane-Toxic Lipids in Vitro," Abstract 2248, *Proceedings of the American Assoc. for Cancer Res.*, 31, 416, Mar. 1990.
Hirsch, M. S. et al., "Antiviral Agents," *Fields Virology*, Third Edition, Lippincott, Raven Publishers, p. 431-466, 1996.
Hong et al., *Journal of Medicinal Chemistry* 33: 1380-1386, 1990.
Hong, C. et al., "Nucleoside Conjugates. 15. Synthesis and Biological Activity of Anti-HIV Nucleoside Conjugates of Ether and Thioether Phospholipids," *Abstract J. Med. Chem.*, vol. 39, No. 9, pp. 1771-1777, 1996.
Hong, C. et al., "Nucleoside-Ether Lipid Conjugates as Biotransformed Prodrugs of Antitumor and Antiviral Nucleosides," *Abstract J. Lipid Mediators Cell Signaling*, vol. 10, No. 1-2, pp. 159-161, 1994.
Hostetler, et al., "Antiviral Activity of Phosphatidyl-Dideooxycytidine in Hepatitis B-infected Cells and Enhanced Hepatic Uptake in Mice," *Antiviral Research,*, 59-65, 1994.
Hostetler et al., "Phosphatidylazidothymidine and Phosphatidyl-ddC: Assessment of Uptake in Mouse Lymphoid Tissues and Antiviral Activities in Human Immunodeficiency Virus-Infected Cells and in Rauscher Leukemia Virus-Infected Mice," *Antimicrobial Agents and Chemotherapy*, Dec. 2792-2797, 1994.
Hostetler et al., "Synthesis and Antiretrovial Activity of Phospholipid Analogs of Azidothymidine and Other Antiviral Nucleosides," *Journal of Biological Chemistry*, 265: 6112-6117, 1990.
Hostetler et al., "Phosphatidlazidothymidine: Mechanism of Antiretroviral Action in CEM Cells," *Journal of Biological Chemistry*, 266: 11714-11717, 1990.
Hruska, J. F. et al., "In Vivo Inhibition of Respiratory Syncytial Virus by Ribavirin," *Antimicr Agents Chemother.*, 21:125-130, 1982.
Hsu, L. et al., "Synthesis of Anti-Restricted Pyrimidine Acyclic Nucleosides," *Journal of Organic Chemistry*, vol. 57, No. 12, pp. 3354-3358, 1992.
IMPACT RSV Study Group, "Palivizumab, a Humanized Respiratory Syncytial Virus Monoclonal Antibody Reduces Hospitalization from Respiratory Syncytial Virus Infection in High-Risk Infants," *Pediatrics*, 102:531-537, 1998.
Jahne et al., "Preparation of Carbocyclic Phosphonate Nucleosides," *Tetrahedron Letters*, vol. 33, No. 37, 5335-5338, 1992.
Jayasuriya et al., Design, Synthesis, and Activity of Membrane-Disrupting Bolaphiles, *J. Am. Chem. Soc.*, 112, 5884-5850, 1990.
Jia et al., "Diamide Analogues of Phosphatidylcholine as Potential Anti-AIDS Agents," *J. Chem. Soc.*, 2521-2523, 1993.
Kakiuchi N. et al., "Non-peptide Inhibitors of HCV Serine Proteinase," *J. FEBS Letters*, 421:217-220, 1993.
Kasnar, B. et al., "Synthesis of 2',3'-Dideoxy- and 3'-Azido-2',3'Dideoxy-Pyridazine Nucleosides as Potential Antiviral Agents," *Nucleosides & Nucleotides*, 13(1-3), pp. 459-479, 1994.
Kawana, F. et al., "Inhibitory Effects of Antiviral Compounds on Respiratory Syncytial Virus Replication In Vitro" *Antimicrob Agents Chemother.*, Aug. 31, (8):1225-30, 1987.
Korba, B. E. et al., "Use of a Standardized Cell Culture Assay to Assess Activities of Nucleoside Analogs Against Hepatitis B Virus Replication," *Antiviral Research*, 19, 55-70, 1992.
Krugner-Higby, L., et al., "Membrane-Interactive Phosphilipids Inhibit HIV Type 1-Induced Cell Fusion and Surface gp160/gp120 Binding to Monoclonal Antibody," *AIDS Research and Human Retroviruses*, vol. 11, 705-712, 1995.
Krugner-Higby, L. A. et al., "Novel Membrane Interactive Ether Lipid Analogs Inhibit HIV-1 Glycoprotein Interaction with CD4+ Cells," Abstract 321, 32nd *Interscience Conf. on Antimicrobial Agents and Chemotherappy*, Anaheim, 164, Oct. 11-14, 1992.
Kucera, L. S., et al., "Activity of Triciribine and Triciribine-5'-Monophosphate Against Human Immunodeficiency Virus Types 1 and 2k" *Aids Research and Human Retroviruses*, vol. 9, No. 4, pp. 307-314, 1993.
Kucera, "Effect of Membrane-Active Ether Lipid (EL) Analogues on Human Immunodeficiency Virus Production Measured by Plaque Assay," *Annuals of the New York Academy of Sciences*, 545-548, Dec. 26, 1990.
Kucera, "Inhibition of HIV-1 Plaque Formation by a Novel Class of Membrane-Active Ether Lipid Analogs," *International Conference on AIDS*, Abstract No, W.C.O.21, p. 528, Jun. 4-9, 1989.
Kucera, "Inhibition of Human Immunodeficiency Virus-1 (HIV-1) by Novel Membrane Interactive Ether Lipids," Abstract No. 2470, *Proceedings of the American Assoc. for Cancer Res.*, 31, 416, Mar. 1990.
Kucera, L., et al., "Inhibition of Human Immunodeficiency Virus Envelope Glycoprotein-Mediated Cell Fusion by Synthetic Phospholipid Analogs," *Antiviral Research*, p. A260, 1985.
Kucera, "Investigations on Membrane Activity Ether Lipid Analogs that Alter Functional Expression of HIV-1 Induces Glycoproteins and Inhibit Pathogenesis," Abstract, *Innovations in Therapy of Human Viral Diseases, Symposium, Research Triangle Park*, 16, Dec. 6-9, 1992.
Kucera, L.S. et al., "In Vitro Evaluation and Characterization of Newly Designed Alkylamidophospholipid Analogues as Anti-Human Immunodeficiency Virus Type 1 Agents," *Antiviral Chemistry and Chemotherapy*, 9:157-165, 1998.

Kucera, L. et al., "Novel Ether Lipid Analogs of Platelet Activating Factor with Anti-Hepatitis B Virus Activity," Abstract, *ICAAC Orlando*, 1994.

Kucera, L. et al, "Novel Membrane-Interactive Ether Lipid Analogs That Inhibit Infectious HIV-1 Production and Induce Defective Virus Formation," *AIDS Research and Human Retroviruses*, 6, 491-501, 1990.

Kumar, R., et al, "Equal Inhibition of HIV Replication by Steroisomers of Phosphatidyl-Azidothymidine—Lack of Stereospecificity of Lysosomal Phospholipase $A_1$," *The Journal of Biological Chemistry*, 267, 20288-20292, 1992.

Larder et al., *Science* 243: 1731-1734, 1989.

Lister et al., "Cyclopentanoid Analogs of Phosphatidylcholine: Susceptibility to Phospholipase $A_2$," *Journal of Lipid Research*, vol. 29, 1297-1308, 1988.

Maccjak, D. J. et al., "Inhibition of Viral Replication by Nuclease Resistant Hammerhead Birozymes Directed Against Hepatitis C virus RNA," *Hepatology*, 30 Abstract 995, 1999.

M. MacCoss et al., "Synthesis and Biological Activity of Novel Nucleoside-Phospholipid Prodrugs," *4th International Round Table Nucleosides, Nucleotides and their Biological Applications*, Antwerp, Feb. 4-6, p. 255-263, Feb. 4-6, 1981.

Marasco, Jr., C. J., "The Synthesis and Biological Activity of Novel Alkylglycerol Derivatives as Inhibitors of Protein Kinase C Activity, Neoplastic Cell Growth, and HIV-1 Infectivity," *Dissertation for Ph.D., Univ. of No. Carolina*, Chapel Hill, 1990.

Marasco, C. J. et al., "Synthesis and Biological Activity of Novel Quaternary Ammonium Derviatives of Alkylglycerols as Potent Inhibitors of Protein Kincase C," *Journal of Medicinal Chemistry*, No. 33, pp. 985-992, Mar. 1990.

Marasco et al., "The Synthesis and Biological Testing of Alkyl Glycerols as Potential Inhibitors of Protein Kinase C," *American Assoc. of Pharmaceutical Scientists Abstract*, vol. 9, No. 10, 1992.

Marx, M. H. et al., "Synthesis and Evaluation of Neoplastic Cell Growth Inhibition of 1-*N*-Alkylamide Analogues of Glycero-3-Phosphocholine," *Journal of Medicinal Chemistry*, Abstract, 31, 858-863, Mar. 28, 1988.

Meert, K. L. et al., "Aerosolized Ribavirin in Mechanically Ventilated Children with Respiratory Syncytial Virus Lower Respiratory Tract Disease: a Prospective Double-Blind Randomized Trial," *Crit Care Med.*, Abstract 22:566-572, Apr. 1994.

Mertes et al., "Charge-Spatial Models. cis- and trans-3- and -4-Substituted Cyclohexyl Phosphates as Analogs of 2'- Deoxyuridine 5'-Phosphate," *J. Med. Chem.*, vol. 12(5), 828-832, 1968.

Meyer, K. L., et al., "In Vitro Evaluation of Phosphocoline and Quaternary Ammonium Containing Lipids as Novel Anti-HIV Agents," *J. Med. Chem*, 34, 1377-1383, 1991.

Meyer, "Synthesis and Evaluation of Anti-HIV-1 Ether Lipids," *AAPS Meeting*, Atlanta Abstract N. MN-510, p. S-41, Oct. 22-25, 1989.

Miller, R. H., et al., "Common Evolutionary Orgin of Hepatitis B Virus and Retroviruses," *Proc. Natl. Acad. Sci.* USA, 83, pp. 2531-2535, Apr. 1986.

Mitsuya, H. et al., "Strategies for Antiviral Therapy in AIDS," *Nature*, 325, 773-78, Feb. 26, 1987.

Modest, "Combination Chemotherapy Studies with Antitumor and Antiviral Ether Lipid Analogs," Abstract 2471, *Proceedings of the American Assoc. for Cancer Res.*, 31, 416 Abstract 2471, Mar. 1990.

Modest, E., et al., "Comparison of Cell Kill Induced by Two Ether Lipids in Combination with Hyperthermia," *Proceedings of the American Association for Cancer Research; Preclinical Pharmacology Experimetal Therapeutics*, vol. 31, pp. 416, Abstract 2467, Mar. 1990.

Modest, E. J. et al., "Pharmacological Effects and Anticancer Activity of New Ether Phospholipid Analogs," *The Pharmacological Effect of Lipids III: Role of Lipids in Cancer Research*, (IN PRESS), pp. 330-337, 1989.

Molla, A. et al., "Human Serum Attenuates the Activity of Protease Inhibitors Toward Wild-Type and Mutant Human Immunodeficiency Virus," *Virology*, 250:255-262, 1988.

Morrey, J. D. et al., "Effects of Zidovudine on Friend Virus Complex Infection in Rfv-$3^{r/s}$ Genotype-Containing Mice Used as a Model for HIV Infection," *Journal of Acquired Immune Deficiency Syndromes*, 3, 500-10, 1990.

Morris-Natschke, S. L. et al., "Synthesis of Phosphocholine and Quaternary Amine Ether Lipids and Evaluation of in Vitro Antineoplastic Activity," *J. Med. Chem.*, 36:2018-2025, 1993.

Morris-Natschke, S. et al. "Synthesis of Sulfur Analogues of Alkyl Lysophospholipid and Neoplastic Cell Growth Inhibitory Properties," *J. of Med. Chem.*, 29, 2114-17, 1986.

Mutson, M. A. et al., "Two Distinct Subtypes of Human Respiratory Syncytial Virus," *The Journal of General Virology*, 66:2111-2124, Oct. 1985.

Nara, P. L. et al., "Simple, Rapid, Quantitative, Syncytium-Forming Microassay for the Detection of Human Immunodeficiency Virus Neutralizing Antibody," *AIDS Research and Human Retroviruses*, 3, 283-302, 1987.

Noseda, A. et al., "In Vitro Antiproliferative Activity of Combinations of Ether Lipid Analogues and DNA-interactive Agents Against Human Tumor Cells," *Cancer Research*, 48, 1788-1791, Apr. 1, 1988.

Noseda, A. et al., "Neoplastic Cell Inhibition with New Ether Lipids Analogs," *Lipids*, 22, 878-883, Nov. 1987.

Ostertag, W. et al., "Induction of Endogenous Virus and of Thymidine Kinase by Bromodeoxyuridine in Cell Cultures Transformed by Friend Virus," *Proc. Nat. Acad. Sci. USA*, 71: 4980-85, Dec. 1974.

Pacheco, D. Y. et al., "Mechanisms of Toxicity of Hepsulfam in Human Tumor Cell Lines," Abstract 2446, *Proceedings of the American Association for Cancer Research*, 81, 412, May 1990.

Painuly et al., "Preparative HPLC of an Experimental Anti-HIV Analogue of AZT: Azidothymidine Monophosphate Diglyceride (AZT-MP-DG)," *Journal of Liquid Chromatography*, 16(11), 2237-2248, 1993.

Pajouhesh et al., "Synthesis of Polar Head Group Homologs of All-trans-cyclopentano-phosphatidlycholine, Phosphatidyl-N, N-Dimethylethanolamine, and Phosphatidylethanolamine," *Journal of Lipid Research*, vol. 25, 294-303, 1984.

Piantadosi, C. et al., "Synthesis and Evaluation of Novel Ether Lipid Nucleoside Conjugates for Anti-HIV-1 Activity," *J. Med. Chem.*, 34, 1408-14, 1991.

Pidgeon, C. et al., "Anti-HIV Drugs Conjugated to the Glycerobackbone of Phospholipids," *The Journal of Biological Chemistry*, 7773-7778, 1993.

Pidgeon C. et al., "Novel Acylated Phospholipid Drugs for AIDS," *Chemical Abstract*, 120:69591, 1994.

The PREVENT Study Group, "Reduction of Respiratory Syncytial Virus Hospitalized Among Premature Infants and Infants with Bronchopulmonary Dysplasia Using Respiratory Syncytial Virus Immune Globulin Prophylaxis," *Pediatrics*, 99:93-99, 1997.

Poiesz et al., *Proc. Natl Acad. Sci.* U.S.A. 77: 7415-7419, 1980.

Prince, G. A., "The Pathogenesis of Respiratory Syncytial Virus Infection in Cotton Rats," *Am J Pathol Abstract.*, 93:771-91, 1978.

Qasim M.A. et al. "Interscaffolding Additivity. Association of $P_1$ Variants of Eglin c and of Turkey Ovomucoid Third Domain with Serine Proteinases,", *Biochemistry* 36:1598-1607, 1997.

Qui et al., "Membrane Properties of Antiviral Phospholipids Containing Heteroatoms in the Acyl Chains," *Biochemistry*, 33(4), 960-72, 1994.

C. Raetz et al., "Phospholipid Derivative of Cytosine Arabinoside and its Conversion to Phosphatidylinositol by Animal Tissue," *Science* 196, 303-304, 1977.

Richman et al., *New England Journal of Medicine* 317: 192-197, 1987.

Rodriguez, W. J. et al., "Prospective Follow-Up and Pulmonary Functions from a Placebo-Controlled Randomized Trial of Ribavirin Therapy in Respiratory Syncytial Virus Bronchiolitis," *Arch Pediatr Adolesc Med*, 153:469-474, May 1999.

Runge et al., "Destruction of Human solid Tumors by Alkyl Lyso Phospho Lipids," *Journal of the National Cancer Institute*, vol. 64, 1301-1306, 1980.

Sable, C. A. et al., "Orthomyxoviral and Paramyxoviral Infections in Transplant Patients," *Infect Dis Clin North Am*, Abstract, 9:987-1003, Dec. 1995.

Sarin, P. S. et al., "Effects of a Novel Compound (AL 721) on HTLV-III Infectivity in Vitro," *The New England Journal of Medicine*, vol. 313, 1289-90, Nov. 14, 1985.

Scolaro M. J. et al., "Inhibition of Virus Replication with Oligonucleotides," Chemical Abstracts, 117:124476, 1992.

Sidoti et al., "Cytostatic Activity of New Synthetic Anti-Tumor AZA-Alkyllsophospholipids," *Int. J. Cancer* 51, 712-717, 1992.

Small, "Characterization of Cells Sensitive and Resistant to ET-18-OCH," Abstract 2447, *Proceedings of the American Assoc. for Cancer Res.*, 31, 416, Mar. 1990.

Smith, D. W. et al., "A Controlled Trial of Aerosolized Ribavirin in Infants Receiving Mechanical Ventilation for Severe Respiratory Syncytial Virus Infection," *New England Journal of Medicine*, 325:24-29, Jul. 1991.

Steim et al., "Lipid Conjugates of Antiretroviral Agents. I. Azidothymidine-Monophosphate-Digylceride: Anti-HIV Activity, Physical Properties, and Interaction with Plasma Proteins," *Biochemical and Biophysical Research Communications*, vol. 171, No. 1, 451-457, 1990.

Sudo K. et al., "Inhibitory Effects of Podphyllotoxin Derivatives on Herpes Simplex Virus Replication;" *Antiviral Chemistry and Chemotherapy* 9:186, 1998.

Sudo K. et al., "Establishing of an In Vitro System for Screening Hepatitis C Virus Protease Inhibitors Using High Performance Liquid Chromatography," *Antiviral Research* 32:9-18, 1996.

Sunamoto, J. et al., "Induction of Cytotoxic T Cell," *Chemical Abstracts*, 117:68365, 1992.

Surbone et al., *Annals of Internal Medicine*, 108: 534-540, 1988.

Surles, J. R. et al, "Multigram Synthesis of 1-Alkylamido Phospholipids," *Lipids*, 28, 55-57, 1993.

Swayze, E. E., et al., "Synthesis of 1-(2-Aminopropyl) Benzimidazoles, Structurally Related to the Tibo Derivative R82150, With Activity Against Human Immunodeficiency Virus," *Bioorganic & Medical Chemistry Letters*, vol. 3, No. 4, pp. 543-546, 1993.

Takeshita N. et al., "An Enzyme-Linked Immunosorbent Assay for Detecting Proteolytic Activity of Hepatitis C Virus Proteinase," *Analytical Biochemistry* 247:242-246, May 1, 1997.

Tarnowski et al, "Effect of Lyso Lecithin and Analogs on Mouse Ascites," *Cancer Research*, vol. 38, 339-344, 1978.

Thompson, J., et al., "Phospholipid Analog Inhibition of Human Immunodeficiency Virus Envelope Glycoprotein-Mediated Cell Fusion," *Abstracts of 2nd National Conference on Human Retroviruses*, Session 18, 1995.

Tiollais, P., et al., "Hepatitis B. Virus," *Scientific American*, 116-123, Apr. 1991.

Van Wijk et al., "Synthesis and Antiviral Activity of 3'-azido-3'deoxythymidine Triphosphate Distearolyglycerol: A Novel :Phospholipid Conjugate of the Anti-HIV Agent AZT," *Chemistry and Physics of Lipids*, 70, 213-222, 1994.

Van Wijk, G. M. et al., "Spontaneous and Protein-Mediated Intermembrance Transfer of the Antiretroviral Liponucleotide 3'-Deoxythymidine Diphosphate Diglyceride," *Biochemistry*, 31, 5912-5917, Jun. 30, 1992.

Vos, G. D. et al., "Treatment of Respiratory Failure Due to Respiratory Syncytial Virus Pneumonia with Natural Surfactant," *Pediatr Pulmonol.*, Abstract 22:412-415, Dec. 1996.

Wang, E. E. et al., "Pediatric Investigators Collaborative Network on Infections in Canada (PICNIC) Prospective Study of Risk Factors and Outcomes in Patients Hospitalized with Respiratory Syncytial Viral Lower Respiratory Tract Infection," Abstract, *J Pediatr*, 126:212-219, Feb. 1995.

Whimbey, E. et al., "Community Respiratory Virus Infections Among Hospitalized Adult Bone Marrow Transplant Recipients," Abstract, *Clin Infect Dis.*, 22:778-782, May 1996.

Yamaue, H. et al., "Chemosensitivity Testing with Highly Purified Fresh Human Tumor Cells with the MTT Colorimetric Assay," Abstract, *Eur J Cancer*, 27:1258-1263, 1991.

Yanagawa, H. et al."Spontaneous Formation of Superhelical Strands," *Journal of the American Chemical Society*, 111, 4567-70, Jun. 21, 1989.

Yarchoan, R. et al., "Therapeutic Strategies in the Treatment of AIDS," *Annual Reports in Medicinal Chemistry*, vol. 23, 253-263, 1988.

\* cited by examiner lipid & ara-C coupled through phosphate ester lipid & gemcitabine coupled through phosphate ester lipid & ara-C coupled through phosphonate ester lipid & gemcitabine coupled through phosphonate ester lipid coupled to methotrexate through an ester

COMPOSITIONS AND METHODS FOR TARGETING CANCER CELLS

CROSS REFERENCE TO RELATED APPLICATIONS

This application is a divisional of U.S. application Ser. No. 09/693,658 filed Oct. 19, 2000, now U.S. Pat. No. 6,670,341.

STATEMENT REGARDING FEDERALLY SUPPORTED RESEARCH AND DEVELOPMENT

This research was supported in part by U.S. Government funds (National Cancer Institute Grant No. CA12197), and the U.S. Government may therefore have certain rights in the invention.

BACKGROUND OF THE INVENTION

Acquired immunodeficiency syndrome (AIDS) is a degenerative disease of the immune system and central nervous system (CNS) resulting from infection of humans by HIV virus. AIDS is responsible for a rapidly growing fatality rate in the world population. At present, no cure has been found, and clinically approved drugs are limited in number. These drugs include nucleoside reverse transcriptase (RT) inhibitors such as 3'-azido-3'-deoxythymidine (AZT, Zidovudine), dideoxyinosine (ddI, Didanosine), dideoxycytidine (ddC, Zalcitabine), 2',3'-dideoxy-3'-thiacytidine (3TC, Lamivudine), and 2',3'-didehydro-3'-deoxythymidine (d4T, Stavudine), a non-nucleoside RT inhibitor (Niverapine), and protease inhibitors such as saquinavir (Inverase), ritonavir (Norvir), indinavir (Crixivan), and nelfinavir (Viracept). Nucleoside RT inhibitors generally have similar structures (2',3'-dideoxynucleosides) and act at an early stage in virus replication to inhibit provirus DNA synthesis (De Clercq, 1995, Journal of Medicinal Chemistry, 38:2491-2517). However, AZT, the recommended initial therapeutic agent, and the other nucleoside analogues have several limitations, including adverse side effects such as bone marrow depression and anemia (Gill et al., 1987, Annals of Internal Medicine, 107:502-505; Richman et al., 1987, New England Journal of Medicine, 317:192-197). Peripheral neuropathy is also a major and common side effect. AZT is rapidly eliminated from the plasma with a half-life of about one hour (Surbone et al., 1988, Annals of Internal Medicine, 108:534-540) and is quickly metabolized in the liver to its corresponding 5'-glucuronide, which is inactive.

Presently, only a small number of antiviral drugs are available for treatment of virus infections. A complication to the development of such drugs is that mutant strains of virus which are resistant to currently available antiviral drugs are developing at an alarming rate. Combinations of new drugs having unique modes of action are urgently needed to replace drugs that have lost their potency against viruses as a result of virus mutations. A further complication to the development of antiviral drugs is that development of viral resistance to available compounds is not the same in different body compartments and fluids. For example, evolution of drug resistance among HIV-1 clinical isolates is often discordant in blood and semen of HIV-1 positive males (Eron et al., 1998, AIDS 12:F181-F189).

Further, currently available drugs useful for antiviral therapy sometimes ineffectively penetrate the genital tract. This is a serious drawback to the use of these drugs to combat viruses which infect the genital tract. If an antiviral drug promotes development of resistance in the genital tract and the virus is commonly transmitted from this body site, the drug will rapidly become ineffective for treatment of the virus infection in the population at risk for transmission. Hence, drug-resistant mutants of certain viruses can be rapidly spread by sexual contact in the human population. It is known that viruses such as HIV, hepatitis B, hepatitis C, herpes simplex virus, cytomegalovirus, papilloma viruses, and many others are transmitted via sexual contact by both males and females. Thus, therapeutic drugs that fully suppress virus infections in the genital tract are a high public health priority.

Another limitation of presently available antiviral drugs is that rapid emergence of drug resistant mutant virus can lead to decreased sensitivity to the drug within a patient or within a patient population (Larder et al., 1989, Science, 243:1731-1734). Thus, the beneficial effects of drugs such as AZT are limited in duration.

The anti-HIV chemotherapy era which started a decade ago has recently made significant progress toward better control of HIV-1 infection by the introduction of protease inhibitors and the use of combinations of nucleoside and non-nucleoside RT inhibitors with protease inhibitors. Monotherapy (e.g. administration of a single drug) using a nucleoside or non-nucleoside RT inhibitor or a protease inhibitor is no longer a recommended form of therapy for treatment of a patient with a virus infection such as HIV-1 infection. Although combinations of AZT, 3TC, and a protease inhibitor have reduced virus load in the plasma of patients to below detectable levels (i.e. fewer than 200 copies of viral RNA per milliliter of plasma) with a concomitant increase in $CD4^+$ cell count, some drug combinations have been associated with increased toxicity in a person receiving multiple drug therapies. Also, although reduction in virus burden in the plasma of patients to non-detectable levels achieved using some drug combinations is impressive, drug resistance is an escalating problem due to both use and misuse of drug therapy (De Clercq, 1995, Journal of Medicinal Chemistry, 38:2491-2517; Bartlett, 1996, Infectious Diseases in Clinical Practice, 5:172-179) and evolution of resistant mutants in blood and seminal fluids (Eron et al., 1998, AIDS, 12:F181-F189).

The pathogenic events in HIV disease have recently been reviewed by Fauci (1996, Nature {New Biology}, 384:529-534). The current understanding is that entry of HIV into cells varies with the virus strain and cell type. Primary infection of humans is associated with macrophage tropic (M-tropic) virus that utilize the CD4 receptor and a beta-chemokine co-receptor (CCR5) for entry into macrophages. As HIV infection progresses, the initial M-tropic viruses are usually replaced by T-tropic viruses that enter T-lymphocytes via the CD4 receptor and co-receptor CXCR4 (fusin). The viral determinant of cellular tropism maps to the gp 120 subunit of HIV-1 Env protein, particularly the 3rd variable region or V3 loop of gp120. Upon entry into these cells, HIV probably infects dendretic cells, which then carry the virus to CD4+ cells in the lymphoid organs. Infection is then established in the lymphoid organs and a burst of infectious virus seeds itself throughout the body, including the CNS, brain, and lymphoid tissues and sexual organs (e.g. testes). Current drugs used in therapies for HIV infection and AIDS noted above have a limited capacity and half-life for absorption from the stomach to the blood, accumulation into lymphoid organs, crossing the blood-brain barrier into the CNS, or entering the sexual organs (e.g. testes) to attack sanctuaries for HIV replication.

Synthetic phosphocholine lipid (PC lipid) analogues such as, for example, 1-decanamido-2-decyloxypropyl-3-phosphocholine (INK-11) have demonstrated a low incidence of unwanted side effects in mice such as reduction of bone marrow precursor cells and have exhibited high differential selectivity (i.e. the ratio of $TC_{50}$ for cytotoxicity to $EC_{50}$ for antiviral activity, DS=1342 for INK-11) in human leukocytes in cultured cells. At a dosage of 50 milligrams per kilogram of body weight per day for 21 days, INK-11 inhibited Friend leukemia virus-(FLV-) induced pathogenesis by 42% in infected mice, as indicated by significant activity against splenomegaly. The observation that use of INK-11 resulted in only moderate suppression against RT activity compared with AZT alone (42% vs 98%, respectively) suggests that INK-11 induces production of defective virus, similar to the effect achieved using other lipid compounds alone (Kucera, et al., 1990, AIDS Research & Human Retroviruses 6:491-501).

Other synthetic phospholipids which do not comprise a phosphocholine moiety (non-PC lipids) have been conjugated with antiviral chemotherapeutic agents. For example, thioether lipid-nucleoside conjugates have exhibited improved antineoplastic activity in tumor-bearing mice (Hong et al., 1990, Journal of Medicinal Chemistry 33:1380-1386). Also, natural phospholipids coupled to AZT or to dideoxynucleosides (ddT, ddC) have proven to be markedly active against HIV by inhibiting viral RT activity (Steim et al., 1990, Biochemical & Biophysical Research Communications 171:451-457; Hostetler et al., 1990, Journal of Biological Chemistry 265:6112-6117; Hostetler et al., 1991, Journal of Biological Chemistry 266:11714-11717). Studies of phospholipid antiviral efficacy have also included chemically conjugating AZT or ddI, through a phosphate-ester bond, to selected synthetic phosphatidic acid lipid analogues (Piantadosi et al., 1991, Journal of Medicinal Chemistry 34:1408-1414). Synthetic phosphate-ester linked lipid-nucleoside conjugates were found to be markedly active against infectious HIV-1 production in both acutely- and persistently-infected cells, and were 5- to 10-fold less cytotoxic compared with AZT alone (Piantadosi et al., 1991, Journal of Medicinal Chemistry 34:1408-1414). Results of preliminary studies indicated that synthetic lipid-AZT conjugates block reactivity of HIV-1-induced gp160/gp120 proteins with specific monoclonal antibodies on the surface of infected and treated cells and on the surface of treated HIV-1 particles, as measured by flow cytometry. These conjugate compounds also caused inhibition of HIV-1-induced cell fusion (Kucera et al., 1992, In: Novel Membrane Interactive Ether Lipids With Anti-Human Immunodeficiency Virus Activity, Aloia et al., eds., Membrane Interactions of HIV, pp. 329-350; Krugner-Higby et al., 1995, AIDS Research & Human Retroviruses 11:705-712). However, these phosphate ester-linked lipid-AZT conjugates (non-PC lipid-AZT conjugates) were not very active against AZT-resistant clinical isolates of HIV-1. Moreover, after intracellular metabolism of the conjugate with resulting release of AZT-monophosphate, the lipid moiety exhibited only moderate to non-detectable antiviral activity (Piantadosi et al., 1991, Journal of Medicinal Chemistry 34:1408-1414).

As with the antiviral agents, the development of anticancer agents for treating cancer effectively has also been problematic. Barriers such as cellular mechanisms of anticancer drug resistance, overcoming the blood-brain barrier to provide adequate delivery of drug to the brain and CNS, inadequate uptake of drug by lymphoid and hematopoietic tissues, toxicity, achieving oral bioavailability, overcoming short drug half-life, and preventing extracellular metabolism of the anticancer agent are faced by the skilled artisan.

In order to improve bioavailability to CNS and brain tissue, nucleoside analogues have been encapsulated in liposomes or used with modifying agents to disrupt the blood-brain barrier (Braekman, et al., 1997, Proc. Amer. Soc. for Clinical Oncology, Abstract #810). Implantable devices have been used to provide more sustained drug delivery to increase the pharmacokinetics of anticancer agents (Del Pan, et al., 1997, Proc. Amer. Soc. for Clinical Oncology, Abstract #1384). Additionally, attempts to improve the efficacy of nucleoside analogues in cancer therapy have included the use of multidrug combinations and high-dose nucleoside analogue therapy (Capizzi, 1996, Investigational New Drugs 14:249-256). None of these methods have adequately overcome the problems discussed above with regard to anticancer agents.

Another attempt to circumvent the problems associated with conventional nucleoside analogue cancer therapy has been the conjugation of these molecules to phospholipids. Thus far, the conjugation of nucleoside analogues to phospholipid molecules has focused on ara-C and a limited number of diacyl, alkylacyl and thioether phospholipids (Hong, 1990, Cancer Res. 50:4401-4406). Although these conjugates have shown efficacy in the treatment of hematologic malignancies, these drugs must be administered intraperitoneally or intravenously and do not overcome the problems discussed above regarding anticancer agents. These conjugates are degraded by phospholipase A and phospholipase B extracellularly and do not provide the option of oral administration.

Despite the promising attributes of compounds such as PC lipids, and non-PC lipid-nucleoside analogue conjugates, currently available antiviral and anticancer agents such as nucleoside analogues and anti-HIV nucleoside drugs have severe inherent limitations. Although such drugs are capable of delaying the onset of symptoms of virus infection and extending survival time for patients, new compounds having the attributes of increased tolerability, potency, and selectivity against specific viruses, differential mechanisms of action, ability to cross the blood-brain barrier, and freedom from myelosuppressive side effects are urgently needed for improved treatment of virus infections. Also, new antiviral and anticancer compounds are needed which more effectively combat cancers or target multiple aspects of the virus life cycle, which facilitate delivery of an anticancer agent to cells and tissues not normally accessible to anticancer agents (e.g. CNS and lymphoid tissues), which combine lipophilic (e.g. phospholipid) and antiretroviral or anticancer agents within the same molecule (e.g. conjugate compounds) in order to yield a drug with a more sustained antiviral or anticancer effect, which decrease the rate of emergence of drug-resistant virus strains, and which inhibit virus replication in a wider range of cellular or tissue reservoirs of virus infection. The present invention satisfies these needs.

BRIEF SUMMARY OF THE INVENTION

The invention includes a compound having the structure of Formula I:

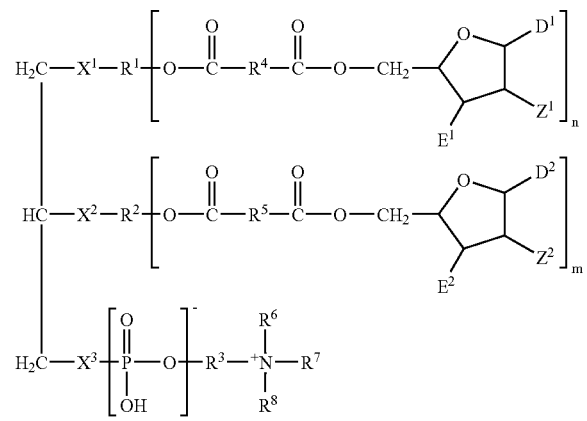

wherein, n and m are each independently 0 or 1, but n and m are not both 0;

$R^1$ is ($C_1$-$C_{16}$) alkyl, branched alkyl, alkenyl or alkynyl if n is 0 and ($C_1$-$C_{16}$) alkylene, branched alkyl, alkenyl or alkynyl if n is 1;

$R^2$ is ($C_1$-$C_{16}$) alkyl branched alkyl alkenyl or alkynyl if m is 0 and ($C_1$-$C_{16}$) alkylene, branched alkyl, alkenyl or alkynyl if m is 1;

$R^3$, $R^4$ and $R^5$ are each independently ($C_1$-$C_8$) alkylene;

$R^6$, $R^7$ and $R^8$ are each independently ($C_1$-$C_8$) alkyl;

$X^1$ and $X^2$ are each independently S, O, NHC=O, OC=O or NH;

$X^3$ is O or S;

$E^1$ is H, S, halo or $N_3$;

$Z^1$ is H, S, or halo; or $E^1$ and $Z^1$ together are a covalent bond;

$E^2$ is H, S, halo, or $N_3$;

$Z^2$ is H, S, or halo; or $E^2$ and $Z^2$ together are a covalent bond;

$D^1$ and $D^2$ are each independently selected from the group consisting of purine, pyrimidine, adenine, thymine, cytosine, guanine, hypoxanthine, inosine, uracil and ring modifications thereof, including O, N, and S substitutions, and wherein, each alkyl, alkylene, branched alkyl, alkenyl, alkynyl, adenine, thymine, cytosine, guanine, pyrimidine, purine, hypoxanthine, inosine and uracil of $R^1$, $R^2$, $R^3$, $R^4$, $R^5$, $R^6$, $R^7$, $R^8$, $D^1$, and $D^2$ can, optionally, be substituted with 1, 2, 3, or 4 substituents independently selected from the group consisting of halo, nitro, trifluoromethyl, ($C_1$-$C_8$) alkyl, ($C_1$-$C_8$) alkoxy, aryl, and N($R^a$)($R^b$) wherein $R^a$ and $R^b$ are each independently selected from the group consisting of H and ($C_1$-$C_8$) alkyl.

In one aspect, the compound is present in an amount effective to inhibit virus replication in a mammal.

In another aspect, $R^1$ is ($C_6$-$C_{16}$) alkyl if n is 0 or —CH=CH— if n is 1.

In yet another aspect, $R^2$ is ($C_6$-$C_{16}$) alkyl if m is 0 or —CH=CH— if m is 1.

In a further aspect, $R^3$ is —$CH_2CH_2$—.

In one embodiment, $R^4$ is —$CH_2$—.

In another embodiment, $R^5$ is —$CH_2$—.

In yet another embodiment, $R^6$, $R^7$ and $R^8$ are each —$CH_3$.

In one aspect, $X^1$ is S, NHC=O, —NH— or O.

In another aspect, $X^2$ is S, NHC=O or O.

In a further aspect, $X^3$ is O or S.

In another aspect, $E^1$ is $N_3$, S or H.

In one embodiment, $Z^1$ is H or S.

In another embodiment, $E^2$ is $N_3$, S or H.

In a further embodiment, $Z^2$ is H or S.

In one aspect, n is 0 and m is 1.

In another aspect, n is 1 and m is 0.

In yet another aspect, $D^1$ is selected from the group consisting of cytosine, guanine, inosine and thymine.

In a further aspect, $D^2$ is selected from the group consisting of cytosine, guanine, inosine and thymine.

In another aspect, the compound is in the form of a pharmaceutically acceptable salt.

In one embodiment, the compound is present in an amount effective to inhibit virus replication in a mammal.

In a preferred embodiment, $R^1$ is ($C_6$-$C_{16}$) alkyl, branched alkyl, alkenyl or alkynyl; $R^2$ is ($C_4$-$C_{12}$) alkylene; $R^3$ is —$CH_2CH_2$—; $R^5$ is —$CH_2$—; $R^6$, $R^7$ and $R^8$ are each $CH_3$; $X^1$ and $X^2$ are each independently S, O or NHC=O; $E^2$ is H or $N_3$; $D^2$ is selected from the group consisting of thymine, cytosine, guanine and inosine, and wherein each alkyl, branched alkyl, alkylene, alkenyl, alkynyl, thymine, cytosine, guanine, and inosine of $R^1$, $R^2$, $R^3$, $R^5$, $R^6$, $R^7$, $R^8$, and $D^2$ can, optionally, be substituted with 1, 2, 3, or 4 substituents independently selected from the group consisting of halo, nitro, trifluoromethyl, ($C_1$-$C_8$) alkyl, ($C_1$-$C_8$) alkoxy, aryl, and N($R^a$)($R^b$), wherein $R^a$ and $R^b$ are each independently selected from the group consisting of H and ($C_1$-$C_8$) alkyl.

The invention also includes a method of treating a virus infection in a mammal. The method comprises administering to the mammal, in an amount effective to treat the infection, a compound having the structure of Formula I:

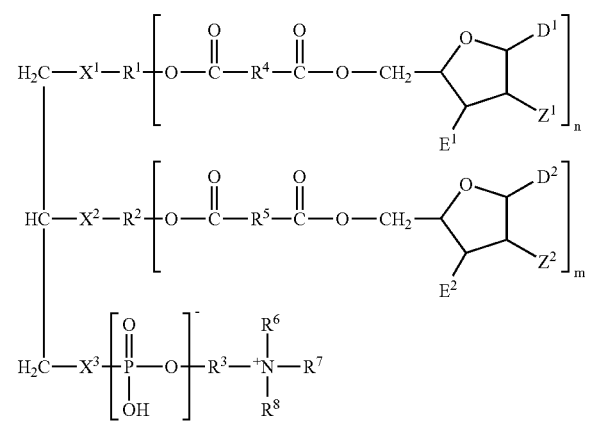

wherein, n and m are each independently 0 or 1, but n and m are not both 0;

$R^1$ is ($C_1$-$C_{16}$) alkyl, branched alkyl, alkenyl or alkynyl if n is 0 and ($C_1$-$C_{16}$) alkylene, branched alkyl, alkenyl or alkynyl if n is 1;

$R^2$ is ($C_1$-$C_{16}$) alkyl, branched alkyl, alkenyl or alkynyl if m is 0 and ($C_1$-$C_{16}$) alkylene, branched alkyl, alkenyl or alkynyl if m is 1;

$R^3$, $R^4$ and $R^5$ are each independently ($C_1$-$C_8$) alkylene;

$R^6$, $R^7$ and $R^8$ are each independently ($C_1$-$C_8$) alkyl;

$X^1$ and $X^2$ are each independently S, O, NHC=O, OC=O or NH;

$X^3$ is O or S;

$E^1$ is H, S, halo or $N_3$;

$Z^1$ is H, S, or halo; or $E^1$ and $Z^1$ together are a covalent bond;

$E^2$ is H, S, halo, or $N_3$;

$Z^2$ is H, S, or halo; or $E^2$ and $Z^2$ together are a covalent bond;

$D^1$ and $D^2$ are each independently selected from the group consisting of purine, pyrimidine, adenine, thymine, cytosine, guanine, hypoxanthine, inosine, uracil and ring modifications thereof, including O, N, and S substitutions, and wherein, each alkyl, alkylene, branched alkyl, alkenyl, alkynyl, adenine, thymine, cytosine, guanine, pyrimidine, purine, hypoxanthine, inosine and uracil of $R^1$, $R^2$, $R^3$, $R^4$, $R^5$, $R^6$, $R^7$, $R^8$, $D^1$, and $D^2$ can, optionally, be substituted with 1, 2, 3, or 4 substituents independently selected from the group consisting of halo, nitro, trifluoromethyl, $(C_1\text{-}C_8)$ alkyl, $(C_1\text{-}C_8)$ alkoxy, aryl, and $N(R^a)(R^b)$ wherein $R^a$ and $R^b$ are each independently selected from the group consisting of H and $(C_1\text{-}C_8)$ alkyl.

In one aspect, $R^1$ is $(C_8\text{-}C_{12})$ alkyl if n is 0 and —$CH_2CH_2$— if n is 1.

In another aspect, $R^2$ is $(C_8\text{-}C_{12})$ alkyl if m is 0 and —$CH_2CH_2$— if m is 1.

In yet another aspect, $R^3$ is —$CH_2CH_2$—.

In one embodiment, $R^4$ is —$CH_2$—.

In another embodiment, $R^5$ is —$CH_2$—.

In a further embodiment, $R^6$, $R^7$ and $R^8$ are each —$CH_3$.

In another embodiment, $X^1$ is S or O.

In one aspect, $X^2$ is S or O.

In another aspect, $X^3$ is O.

In a further aspect, $E^1$ is $N_3$ or H.

In a still further aspect, $Z^1$ is H.

In one embodiment, $E^2$ is $N_3$ or H.

In another embodiment, $Z^2$ is H.

In yet another embodiment, n is 0 and m is 1.

In one aspect, n is 1 and m is 0.

In another aspect, $D^1$ is selected from the group consisting of cytosine, guanine, inosine, and thymine.

In a further aspect, $D^2$ is selected from the group consisting of cytosine, guanine, inosine, and thymine.

In a still further aspect, the virus infection is an infection by a virus selected from the group consisting of HIV, hepatitis virus, and a herpes virus.

In one embodiment, the HIV is selected from the group consisting of HIV-1 and HIV-2.

Preferably, the hepatitis virus is selected from the group consisting of hepatitis A, hepatitis B, hepatitis C, hepatitis D, and hepatitis E viruses.

Preferably, the herpes virus is selected from the group consisting of herpes simplex virus type 1, herpes simplex virus type 2, varicella-zoster virus, cytomegalovirus, Epstein Barr virus, human herpes virus type 6, human herpes virus type 7, and human herpes virus type 8.

In a preferred aspect, $R^1$ is $(C_6\text{-}C_{16})$ alkyl, branched alkyl, alkenyl or alkynyl; $R^2$ is $(C_4\text{-}C_{12})$ alkylene; $R^3$ is —$CH_2CH_2$—; $R^5$ is —$CH_2$—; $R^6$, $R^7$ and $R^8$ are each $CH_3$; $X^1$ and $X^2$ are each independently S, O or NHC=O; $E^2$ is H or $N_3$; $D^2$ is selected from the group consisting of thymine, cytosine, guanine and inosine, and wherein each alkyl, branched alkyl, alkylene, alkenyl, alkynyl, thymine, cytosine, guanine, and inosine of $R^1$, $R^2$, $R^3$, $R^5$, $R^6$, $R^7$, $R^8$, and $D^2$ can, optionally, be substituted with 1, 2, 3, or 4 substituents independently selected from the group consisting of halo, nitro, trifluoromethyl, $(C_1\text{-}C_8)$ alkyl, $(C_1\text{-}C_8)$ alkoxy, aryl, and $N(R^a)(R^b)$, wherein $R^a$ and $R^b$ are each independently selected from the group consisting of H and $(C_1\text{-}C_8)$ alkyl.

In one aspect, a pharmaceutically acceptable salt of the compound is administered to the mammal.

Preferably, the mammal is a human.

The invention also includes a method of inhibiting virus replication in a cell. The method comprises administering to the cell a compound of Formula I in an amount effective to inhibit virus replication in the cell.

The invention includes a pharmaceutical composition comprising a compound of Formula I in combination with a pharmaceutically acceptable carrier.

In one aspect, the compound is present in an amount effective to inhibit virus replication in a mammal.

In another aspect, the compound is present in an amount effective to inhibit virus replication in a mammal.

The invention also includes a kit for treatment of a viral infection in a mammal. The kit comprises a) a composition selected from the group consisting of a compound of Formula I, a pharmaceutically acceptable salt thereof, and a pharmaceutical composition comprising a compound of Formula I, and b) an instructional material.

The invention also includes a kit for inhibition of virus replication in a cell. The kit comprises a) a composition selected from the group consisting of a compound of Formula I, a pharmaceutically acceptable salt thereof, and a pharmaceutical composition comprising a compound of Formula I, and b) an instructional material.

The invention also includes a compound having the structure of Formula III:

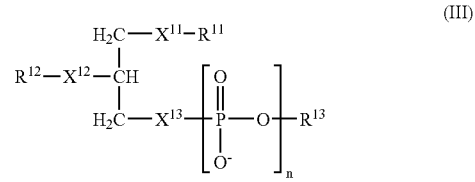

(III)

wherein, $R^{11}$ is $(C_1\text{-}C_{16})$ alkyl, branched alkyl, alkenyl or alkynyl;

$R^{12}$ is $(C_1\text{-}C_{16})$ alkyl, branched alkyl, alkenyl or alkynyl;

$X^{11}$ is O, S, or NHC=O;

$X^{12}$ is O, S, or NHC=O;

$X^{13}$ is O or S;

n is 0, 1 or 2, and $R^{13}$ is a therapeutic agent, wherein, each alkyl, branched alkyl, alkenyl, alkynyl, adenine, thymine, cytosine, guanine, pyrimidine, purine, hypoxanthine, inosine and uracil of $R^{11}$, $R^{12}$, and $R^{13}$ can, optionally, be substituted with 1, 2, 3, or 4 substituents independently selected from the group consisting of halo, nitro, trifluoromethyl, $(C_1\text{-}C_8)$ alkyl, $(C_1\text{-}C_8)$ alkoxy, aryl, and $N(R^a)(R^b)$ wherein $R^a$ and $R^b$ are each independently selected from the group consisting of H and $(C_1\text{-}C_8)$ alkyl, and wherein, if n is 1 or 2, the compound is a phospholipase C substrate and is not a phospholipase A substrate, and further wherein, if n is 1 or 2, the compound is converted to an alkyl lipid and a moiety selected from the group consisting of a nucleoside monophosphate and a nucleoside analogue monophosphate intracellularly in a mammal, and is not converted to an alkyl lipid and a moiety selected from the group consisting of a nucleoside monophosphate and a nucleoside analogue monophosphate extracellularly in a mammal.

In a preferred embodiment, $R^{11}$ is a $C_{12}$ alkyl, branched alkyl, alkenyl or alkynyl; $R^{12}$ is $C_8H_{16}$ alkyl or branched alkyl; n=1, and $R^{13}$ is an anticancer agent selected from the group consisting of gemcitabine, ara-C, 5-azacytidine, cladribine, fludarabine, fluorodeoxyuridine, cytosine arabinoside, 6-mercaptopurine, 6-thioguanine 5-deoxyfluorouridine, ftorafur, capecitabine, 5-deoxy-5-fluorocytidine, 5-aza-cytsine arabinoside, troxacitabine, and pentostatin, wherein the phosphorus atom of the phosphate moiety is covalently linked in a phosphate ester linkage to the oxygen atom of the 5' hydroxyl group of a sugar moiety of $R^{13}$.

The invention also includes a compound having the structure of Formula IV:

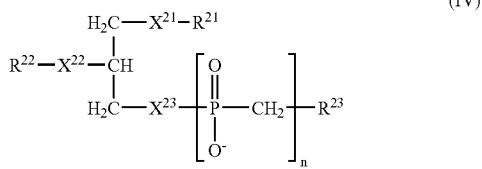

(IV)

wherein, $R^{21}$ is ($C_6$ to $C_{16}$) alkyl, branched alkyl, alkenyl, or alkynyl;

$R^{22}$ is ($C_1$ to $C_{12}$) alkyl, branched alkyl, alkenyl, or alkynyl;

$X^{21}$ is O, S, or NHC=O;

$X^{22}$ is O, S, or NHC=O;

$X^{23}$ is O or S;

n is 1 or 2;

$R^{23}$ is a therapeutic agent, and wherein, each alkyl, branched alkyl, alkenyl, alkynyl, adenine, thymine, cytosine, guanine, pyrimidine, purine, hypoxanthine, inosine and uracil of $R^{21}$, $R^{22}$, and $R^{23}$ can, optionally, be substituted with 1, 2, 3, or 4 substituents independently selected from the group consisting of halo, nitro, trifluoromethyl, ($C_1$-$C_8$) alkyl, ($C_1$-$C_8$) alkoxy, aryl, and $N(R^a)(R^b)$ wherein $R^a$ and $R^b$ are each independently selected from the group consisting of H and ($C_1$-$C_8$) alkyl.

In a preferred aspect, $R^{21}$ is $C_{12}$ alkyl; $R^{22}$ is $C_{10}$ alkyl; n=1, and $R^{23}$ is an anticancer agent selected from the group consisting of gemcitabine, ara-C, 5-azacytidme, cladribine, fludarabine, fluorodeoxyuridine, cytosine arabinoside, 6-mercaptopurine, 6-thioguanine, 5-deoxyfluorouridine, ftorafur, capecitabine, 5-deoxy-5-fluorocytidine, 5-aza-cytsine arabinoside, troxacitabine, and pentostatin, wherein the methylene group of the phosphonate moiety is covalently linked to the oxygen atom of the 5' hydroxyl group of a sugar moiety of $R^{23}$.

The invention also includes a compound having the structure of Formula V:

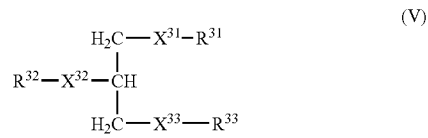

(V)

wherein, $R^{31}$ is ($C_1$ to $C_{16}$) alkyl, branched alkyl, alkenyl, or alkynyl;

$R^{32}$ is ($C_1$ to $C_{16}$) alkyl, branched alkyl, alkenyl, or alkynyl;

$X^{31}$ is O, S, or NHC=O;

$X^{32}$ is O, S, or NHC=O;

$X^{33}$ is —OH, —SH, or amino;

$R^{33}$ is a therapeutic agent, and wherein, each alkyl, branched alkyl, alkenyl, alkynyl, adenine, thymine, cytosine, guanine, pyrimidine, purine, hypoxanthine, inosine and uracil of $R^{31}$, $R^{32}$, and $R^{33}$ can, optionally, be substituted with 1, 2, 3, or 4 substituents independently selected from the group consisting of halo, nitro, trifluoromethyl, ($C_1$-$C_8$) alkyl, ($C_1$-$C_8$) alkoxy, aryl, and $N(R^a)(R^b)$ wherein $R^a$ and $R^b$ are each independently selected from the group consisting of H and ($C_1$-$C_8$) alkyl.

In a preferred embodiment, $R^{31}$ is ($C_6$-$C_{16}$) alkyl, branched alkyl, alkenyl or alkynyl; $R^{32}$ is ($C_1$-$C_8$) alkyl, branched alkyl, alkenyl or alkynyl, and $R^{32}$ is an anticancer agent selected from the group consisting of mitoxanthrone, doxorubicin, idarubicin, epirubicin, daunorubicin, mitomycin, methotrexate, CPT-11, SN-38, camptothecin, topotecan, 9-nitrocamptothecin, and 9-aminocamptothecin, and is covalently linked via an ester, amido or carbamate linkage to the —SH, OH or amino group of $X^{33}$.

In one aspect, the compound is suspended in a pharmaceutically acceptable carrier and is present in an amount effective to combat a cancer in a mammal.

Preferably, the cancer is a cancer selected from the group consisting of a carcinoma, a sarcoma, a neuroblastoma, a leukemia, a lymphoma and a solid tumor.

In one aspect, the compound is present in an amount effective to facilitate delivery of a therapeutic agent to a mammalian cell.

Preferably, the therapeutic agent is an anticancer agent.

Preferably, the cell is in a mammal.

Preferably, the cell is a cell selected from the group consisting of a CNS cell and a lymphoid cell.

In one aspect, the CNS cell is an astrocyte or a glial cell.

In one embodiment, the compound is in the form of a pharmaceutically acceptable salt.

In one aspect, the compound is present in an amount effective to facilitate delivery of a therapeutic agent to a mammalian cell.

In one embodiment, the cell is in a mammal.

Preferably, the cell is a cell selected from the group consisting of a CNS cell and a lymphoid cell.

In one aspect, the compound is present in an amount effective to combat a cancer in a mammal.

In one embodiment, the compound in the pharmaceutically acceptable salt is present in an amount effective to facilitate delivery of a therapeutic agent to a mammalian cell.

Preferably, the therapeutic agent is an anticancer agent.

In one aspect, the cell is in a mammal.

In one embodiment, the cell is a cell selected from the group consisting of a CNS cell and a lymphoid cell.

In one aspect, the compound is present in an amount effective to combat a cancer in a mammal.

The invention also includes a drug delivery agent comprising a pharmaceutical composition. The composition comprises a compound of Formula III or a pharmaceutically acceptable salt thereof, in an amount effective to facilitate delivery of a therapeutic agent to a mammalian cell.

In one aspect, the therapeutic agent is an anticancer agent.

In another aspect, the cell is in a mammal.

Preferably, the cell is a cell selected from the group consisting of a CNS cell and a lymphoid cell.

The invention also includes a drug delivery agent comprising a pharmaceutical composition. The composition comprises a compound of Formula III or a pharmaceutically acceptable salt thereof, in an amount effective to combat a cancer in a mammal.

Preferably, the cancer is a cancer selected from the group consisting of a carcinoma, a sarcoma, a neuroblastoma, a leukemia, a lymphoma and a solid tumor.

The invention also includes a method of facilitating delivery of a therapeutic agent to a mammalian cell. The method comprises administering to the cell a pharmaceutical composition comprising a compound of Formula III or a pharmaceutically acceptable salt thereof, in an amount effective to facilitate delivery of the therapeutic agent to the cell.

In one aspect, the therapeutic agent is an anticancer agent.

In another aspect, the cell is in a mammal.

Preferably, the cell is a cell selected from the group consisting of a CNS cell and a lymphoid cell.

The invention also includes a method of facilitating delivery of a therapeutic agent to a cell. The method comprises administering to the cell a pharmaceutical composition comprising a compound of Formula III or a pharmaceutically acceptable salt thereof, in an amount effective to facilitate delivery of the therapeutic agent to the cell.

In one aspect, the cell is in a mammal.

In another aspect, the cell is a cell selected from the group consisting of a CNS cell and a lymphoid cell.

The invention also includes a method of combating a cancer in a mammal. The method comprises administering to the mammal a pharmaceutical composition comprising a compound of Formula III or a pharmaceutically acceptable salt thereof, in an amount effective to combat a cancer in the mammal.

In one aspect, the cancer is a cancer selected from the group consisting of a carcinoma, a sarcoma, a neuroblastoma, a leukemia, a lymphoma and a solid tumor.

The invention also includes a method of treating a disease in a mammal. The method comprises administering to the mammal a pharmaceutical composition comprising a compound of Formula III, or a pharmaceutically acceptable salt thereof, in an amount effective to facilitate delivery of a therapeutic agent to a cell in the mammal, thereby treating the disease.

In one aspect, the disease is a disease selected from the group consisting of a brain disease, a CNS disease, a lymphatic system disease, a reproductive system disease, a cardiovascular disease, a kidney disease and a liver disease.

The invention also includes a kit for combating a cancer in a mammal. The kit comprises a) a composition selected from the group consisting of a compound of Formula III, a pharmaceutically acceptable salt thereof, and a pharmaceutical composition comprising a compound of Formula III, and b) an instructional material.

The invention also includes a kit for facilitating delivery of a therapeutic agent to a mammalian cell. The kit comprises a) a composition selected from the group consisting of a compound of Formula III, a pharmaceutically acceptable salt thereof, and a pharmaceutical composition comprising a compound of Formula III, and b) an instructional material.

Preferably, the therapeutic agent is an anticancer agent.

BRIEF DESCRIPTION OF THE DRAWINGS

The foregoing summary, as well as the following detailed description of the invention, will be better understood when read in conjunction with the appended drawings.

FIG. 1A depicts the chemical structure of gemcitabine. FIG. 1B depicts the chemical structure of ara-C. FIG. 1C depicts the chemical structure of 5-azacytidine.

FIGS. 5A and 5B, is a pair of formulae depicting the chemical structures of exemplary compounds of Formula III.

FIGS. 6A and 6B, is a pair of formulae depicting the chemical structures of exemplary compounds of Formula IV.

DETAILED DESCRIPTION OF THE INVENTION

Figure 1A:
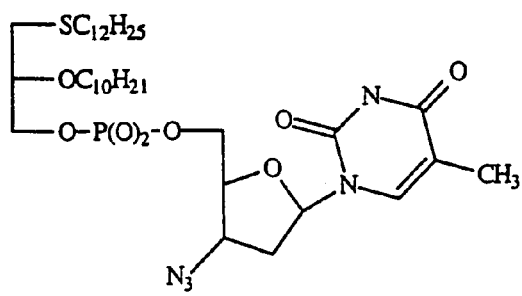
FIGS. 1A, 1B, and 1C is a series of formulae depicting the chemical structures of several anticancer agents.
Figure 1B:
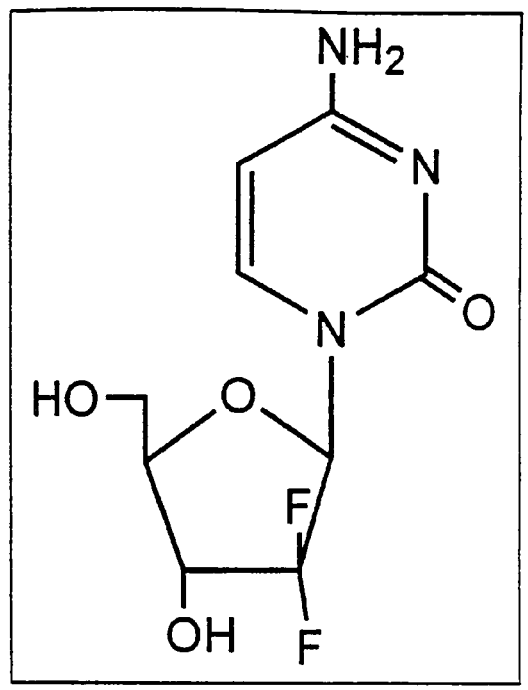
Figure 1C:
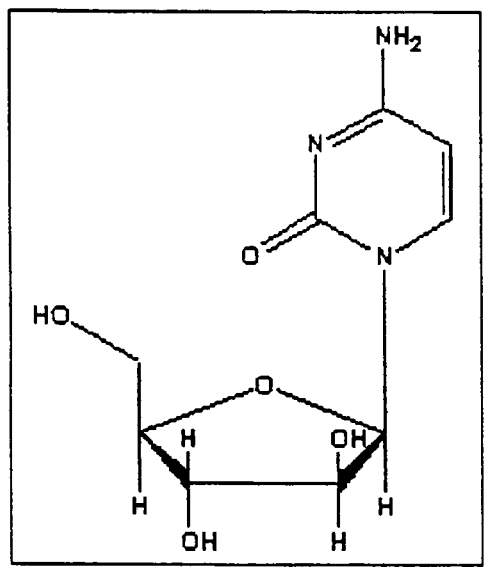
Figure 1D:
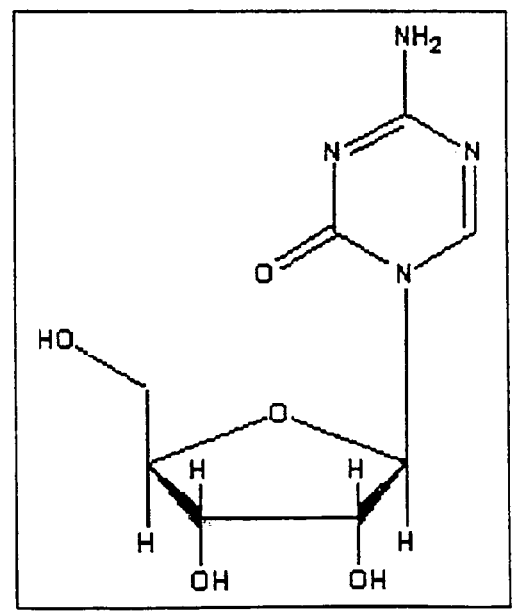
FIG. 1, comprising

The present invention relates to methods and compositions useful in drug delivery for treatment of a virus infection in a mammal by targeting the virus at two or more stages of the virus life cycle and thereby inhibiting virus replication. This mode of use of antiviral compositions is referred to herein as double-targeting a virus infection. The compositions of the invention include compounds comprising at least two chemically combined (e.g. covalently conjugated) antiviral agents which have different modes of action. Because the antiviral agents have different modes of action, they target the virus life cycle at two or more different stages. By way of example and not by limitation, the compositions of the invention include compounds having a nucleoside analogue or protease inhibitor moiety conjugated with a phosphocholine lipid (PC lipid) moiety. Also by way of example and not by limitation, the targets in the viral life cycle of the compounds of the invention may include stages involving reverse transcription, protease activity, and virus assembly. The methods and compositions of the invention are particularly useful in combating drug-resistant mutants of viruses because viruses resistant to nucleoside analogues and protease inhibitors are still sensitive to inhibition by phospholipids.

As used herein, the term "conjugated with" means covalently attached to the same molecule.

The targeted virus may be any type of virus, and non-limiting exemplary viruses include HIV-1, HIV-2, hepatitis virus (e.g. hepatitis A, hepatitis B, hepatitis C, hepatitis D, and hepatitis E viruses), and herpesviruses (e.g. herpes simplex virus types 1 and 2, varicella-zoster virus, cytomegalovirus, Epstein Barr virus, and human herpes viruses types 6, 7, and 8).

The compounds of the invention exhibit biological properties which are superior to currently available antiviral drugs, including (i) reduced cytotoxicity accompanied by the ability of the mammal to tolerate a higher dose of the drug compared with nucleoside analogues or protease inhibitors alone, (ii) ability to target multiple distinct stages of virus replication (e.g. reverse transcription, protease processing of viral proteins and virus assembly, leading to non-replication or to production of defective progeny virus) (iii) ability to simultaneously deliver constant amounts of multiple antiviral agents (e.g. phosphocholine lipid and a nucleoside analogue or phosphocholine lipid and a protease inhibitor) to virus-infected cells with preferential uptake into the CNS, lymphoid tissues, and male and female genital tracts, (iv) intracellular metabolism of the conjugate compound and simultaneous release of two antiviral agents in cells in which virus is multiplying, (v) increased half-life of the compound in vivo compared with nucleoside analogues or protease inhibitors alone, (vi) prolonged duration of biological effect, presumably owing to protection of nucleoside analogue from rapid glucuronide formation in the liver of intact animals, and (vii) capacity to conjugate other small molecular weight compounds to the phosphocholine (PC) lipid backbone for treatment of other diseases of the central nervous system (e.g. Alzheimer's, cancer), in addition to diseases such as AIDS, resulting from virus infection.

Previous studies have established that a PC moiety is an essential component for a phospholipid to exhibit optimal antiviral activity (Piantadosi et al., 1991, J. Med. Chem. 34:1408-1414; Krugner-Higby et al., 1995, AIDS Res. & Human Retrovir. 11:705-712). Compounds comprising phosphatidic acid, phosphoethanolamine, phosphoalkylpyridine, alcohol, or quaternary amine salt moieties were less active, more toxic, exhibited much lower differential selectivities, or some combination of these, relative to the corresponding PC lipids. In certain preferred compounds of the invention, a PC moiety is incorporated into the lipid backbone to result in compounds which exhibit optimal antiviral activity, can accumulate into lymphoid tissues, testes, and vaginal secretions, and can pass the blood-brain barrier into the CNS. These anatomical sites serve as important reservoirs of virus during infection by viruses such as HIV-1, and also serve as sources of transmission of drug-resistant mutants.

The invention also includes methods of treating a virus infection in a cell or in a mammal, such as a human, comprising administering to the cell or mammal a compound of the invention in an amount effective to alleviate or eliminate the virus infection or to alleviate a symptom associated with the infection.

The present invention also includes methods and compositions useful in drug delivery for facilitating delivery of a therapeutic agent to a mammalian cell. As used herein, the term "facilitating delivery" or "to facilitate delivery" of a therapeutic agent to a mammalian cell means enhancing the uptake of a therapeutic agent in a mammalian cell to a level higher than the level of uptake of the therapeutic agent in an otherwise identical mammalian cell which is not administered a compound or composition of the invention. The uptake of a therapeutic agent can be enhanced, by way of example and not by limitation, by any one or more of the following means: by bypassing the requirement for a cellular active transport mechanism for uptake of the therapeutic agent into a cell; by providing the therapeutic agent (i.e. a drug) intracellularly in an activated form, (i.e. the monophosphorylated form in the case of a nucleoside analogue anticancer drug) thereby bypassing the requirement for intracellular activation of the therapeutic agent by an enzyme such as an intracellular kinase; by overcoming a physiological barrier to uptake of the therapeutic agent in a desired cell, such as low solubility, poor absorption from the stomach or small intestine, or impermeability to the blood-brain barrier, to enable delivery of the therapeutic agent to sites not normally accessible thereto (i.e. CNS and lymphoid tissues).

The present invention also includes methods and compositions useful in drug delivery for combating a cancer in a mammal or for treating or alleviating a disease in a mammal.

As used herein, the term "combating a cancer" or "to combat a cancer" in a mammal means, for example, any one or more of the following: to increase survival of a mammal, to decrease or arrest tumor size in a mammal, or to increase the time period of remission of cancer regrowth in a mammal, relative to an otherwise identical mammal which was not administered a composition or compound of the invention.

As used herein, the term "therapeutic agent" means any compound or composition, which, upon entering a mammalian cell, is capable of being of benefit in alleviating or treating a disease in a mammal. By way of example and not by limitation, such compounds and compositions include small organic molecules, peptides, nucleoside analogues, anticancer agents, antiviral agents, ribozymes, antisense oligonucleotides and other drugs. The disease may be any disease experienced by a mammal. By way of example and not by limitation, such diseases include diseases of the brain, CNS, lymphatic system, reproductive system, cardiovascular system, renal system and liver, among others.

As used herein, "alleviating a disease" means reducing the severity of a symptom of the disease.

As used herein, "treating a disease" means reducing the frequency with which a symptom of the disease is experienced by a mammal.

As used herein, the term "anticancer agent" means a therapeutic agent which is capable of exhibiting efficacy at combating a cancer in a mammal or in a mammalian cell, or any compound which is capable of being converted intracellularly to a compound which is capable of exhibiting efficacy at combating a cancer in a mammal or in a mammalian cell.

The mammalian cell can be any type of mammalian cell, including both cancerous and non-cancerous cells. Examples of preferred cells include, but are not limited to, CNS and lymphoid cells. Preferred lymphoid cells include lymphoma, spleen and thymus cells. Preferred CNS cells include brain cells, astrocytes, and glial cells. The cancer can be any type of cancer in a mammal. Preferably, the cancer is one or more of a carcinoma, a sarcoma, a neuroblastoma, a leukemia, a lymphoma and a solid tumor.

The compositions of the invention include compounds which comprise an alkyl lipid or a phospholipid moiety covalently conjugated with a therapeutic agent. As used herein, the term "alkyl lipid" means that portion of any of the compounds of Formulas III, IV and V as described herein without the therapeutic agent moiety.

The invention also includes pharmaceutical compositions and kits for combating a cancer and/or for facilitating delivery of a therapeutic agent to a mammalian cell.

The invention also includes methods which comprise administering a compound of the invention, a pharmaceutically acceptable salt thereof, or a pharmaceutical composition of the invention, in an amount effective to combat a cancer or in an amount effective to facilitate delivery of a therapeutic agent to a mammalian cell.

As used herein, the following terms are defined as follows, unless otherwise described: halo is fluoro, chloro, bromo, or iodo. Alkyl, alkoxy, alkylene, etc. denote both straight and branched groups; but reference to an individual radical such as "propyl" embraces only the straight chain radical, a branched chain isomer such as "isopropyl" being specifically referred to.

The articles "a" and "an" are used herein to refer to one or to more than one (i.e. to at least one) of the grammatical object of the article. By way of example, "an element" means one element or more than one element.

Compounds of the invention having a chiral center can exist in and be isolated in distinct optically active or racemic forms. The present invention encompasses any racemic, optically-active, polymorphic, or stereoisomeric form, or mixtures of such forms of a compound of the invention. Preparation of optically active forms of a compound is well known in the art (for example, by resolution of the racemic form by recrystallization techniques, by synthesis from optically-active starting materials, by chiral synthesis, or by chromatographic separation using a chiral stationary phase). Determination or assessment of antiviral activity can be performed using standard tests described herein or other tests known in the art.

Specific and preferred definitions listed below for radicals and substituents are for illustration only; they do not exclude other defined values or other values within defined ranges for the radicals and substituents described herein.

$C_1$-$C_8$ alkyl moieties include, for example, methyl, ethyl, propyl, isopropyl, butyl, iso-butyl, sec-butyl, pentyl, sec-pentyl, iso-pentyl, hexyl, sec-hexyl, iso-hexyl, heptyl, sec-heptyl, iso-heptyl, and octyl moieties. $C_1$-$C_8$ alkoxy moieties include, for example, methoxy, ethoxy, propoxy, isopropoxy, butoxy, iso-butoxy, sec-butoxy, pentoxy, sec-pentoxy, iso-pentoxy, hexyloxy, sec-hexyloxy, heptoxy, sec-heptoxy, iso-heptoxy, and octyloxy moieties. $C_1$-$C_8$ alkylene moieties include, for example, methylene, ethylene, propylene, iso-propylene, butylene, iso-butylene, sec-butylene, pentylene, sec-pentylene, iso-pentylene, hexylene, sec-hexylene, iso-hexylene, heptylene, sec-heptylene, iso-heptylene, and octylene moieties. $C_6$-$C_{15}$ alkyl moieties include, for example, hexyl, heptyl, sec-heptyl, iso-heptyl, octyl, sec-octyl, iso-octyl, nonyl, sec-nonyl, iso-nonyl, decyl, sec-decyl, iso-decyl, undecyl, sec-undecyl, iso-undecyl, dodecyl, sec-dodecyl, iso-dodecyl, tridecyl, sec-tridecyl, iso-tridecyl, tetradecyl, sec-tetradecyl, iso-tetradecyl, and pentadecyl moieties. $C_6$-$C_{15}$ alkylene moieties include, for example, hexylene, heptylene, sec-heptylene, iso-heptylene, octylene, sec-octylene, iso-octylene, nonylene, sec-nonylene, iso-nonylene, decylene, sec-decylene, iso-decylene, undecylene, sec-undecylene, iso-undecylene, dodecylene, sec-dodecylene, iso-dodecylene, tridecylene, sec-tridecylene, iso-tridecylene, tetradecylene, sec-tetradecylene, iso-tetradecylene, and pentadecylene moieties. $C_8$-$C_{12}$ alkyl moieties include, for example, octyl, sec-octyl, iso-octyl, nonyl, sec-nonyl, iso-nonyl, decyl, sec-decyl, iso-decyl, undecyl, sec-undecyl, iso-undecyl, and dodecyl moieties. $C_8$-$C_{12}$ alkylene moieties include, for example, octylene, sec-octylene, iso-octylene, nonylene, sec-nonylene, iso-nonylene, decylene, sec-decylene, iso-decylene, undecylene, sec-undecylene, iso-undecylene, and dodecylene moieties.

The present invention includes compounds which exhibit antiviral activity and are particularly useful because they exhibit antiviral activity against drug-resistant viruses. Accordingly, the invention includes a compound having the chemical structure of Formula I or a pharmaceutically acceptable salt thereof.

Formula I is

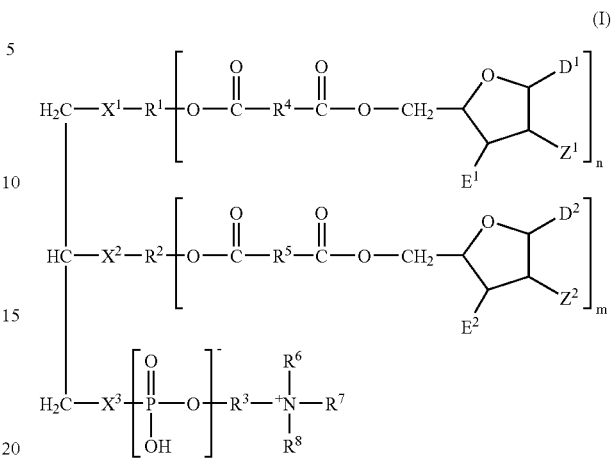

(I)

wherein n and m are each independently 0 or 1, but n and m are not both 0;

$R^1$ is ($C_1$-$C_{16}$) alkyl, branched alkyl, alkenyl or alkynyl if n is 0 and ($C_1$-$C_{16}$) alkylene, alkenyl or alkynyl if n is 1;

$R^2$ is ($C_1$-$C_{16}$) alkyl, branched alkyl, alkenyl or alkynyl if m is 0 and ($C_1$-$C_{16}$) alkylene, alkenyl or alkynyl if m is 1;

$R^3$, $R^4$ and $R^5$ are each independently ($C_1$-$C_8$) alkylene;

$R^6$, $R^7$ and $R^8$ are each independently ($C_1$-$C_8$) alkyl;

$X^1$ and $X^2$ are each independently S, O, NHC=O, OC=O or NH;

$X^3$ is O or S;

$E^1$ is H, S, halo or $N_3$;

$Z^1$ is H, S, or halo; or $E^1$ and $Z^1$ together are a covalent bond;

$E^2$ is H, S, halo, or $N_3$;

$Z^2$ is H, S, or halo; or $E^2$ and $Z^2$ together are a covalent bond, and $D^1$ and $D^2$ are each independently selected from the group consisting of purine, pyrimidine, adenine, thymine, cytosine, guanine, hypoxanthine, inosine, uracil and ring modifications thereof, including O, N, and S substitutions.

In Formula I, each alkyl, alkylene, branched alkyl, alkenyl, alkynyl, adenine, thymine, cytosine, guanine, pyrimidine, purine, hypoxanthine, inosine and uracil of $R^1$, $R^2$, $R^3$, $R^4$, $R^5$, $R^6$, $R^7$, $R^8$, $D^1$, and $D^2$ can, optionally, be substituted with 1, 2, 3, or 4 substituents independently selected from the group consisting of halo, nitro, trifluoro, trifluoromethyl, trifluoromethoxy, ($C_1$-$C_8$) alkyl, ($C_1$-$C_8$) alkoxy, aryl, and $N(R^a)(R^b)$ wherein $R^a$ and $R^b$ are each independently selected from the group consisting of H and ($C_1$-$C_8$) alkyl.

The following are examples of definitions for radicals and substituents of Formula I in preferred embodiments. These examples are not limiting, but are instead provided as examples of several preferred embodiments which are included in the invention.

In preferred embodiments, $R^1$ can be one of ($C_2$-$C_{16}$) alkylene, —$(CH_2)_{12}$—, and —CH=CH—. In these embodiments, $R^1$ is optionally substituted with 1, 2, 3, or 4 substituents selected from the group consisting of halo, nitro, trifluoromethyl, ($C_1$-$C_8$) alkyl, ($C_1$-$C_8$) alkoxy, aryl, and $N(R^a)(R^b)$ wherein $R^a$ and $R^b$ are each independently selected from the group consisting of H and ($C_1$-$C_8$) alkyl.

In preferred embodiments, $R^2$ can be one of $(C_2-C_{16})$ alkylene, $-(CH_2)_8-$, $-(CH_2)_9-$, $-(CH_2)_{10}-$, $-(CH_2)_{11}-$, $-(CH_2)_{12}-$, and $-CH=CH-$. In these embodiments, $R^2$ is optionally substituted with 1, 2, 3 or 4 substituents selected from the group consisting of halo, nitro, trifluoromethyl, $(C_1-C_8)$ alkyl, $(C_1-C_8)$ alkoxy, aryl, and $N(R^a)(R^b)$ wherein $R^a$ and $R^b$ are each independently selected from the group consisting of H and $(C_1-C_8)$ alkyl.

$R^3$ is preferably $-CH_2CH_2-$, optionally substituted with 1, 2, 3, or 4 substituents selected from the group consisting of halo, nitro, trifluoromethyl, $(C_1-C_8)$ alkyl, $(C_1-C_8)$ alkoxy, aryl, and $N(R^a)(R^b)$ wherein $R^a$ and $R^b$ are each independently selected from the group consisting of H and $(C_1-C_8)$ alkyl.

$R^4$ is preferably $-CH_2-$, optionally substituted with 1 or 2, substituents selected from the group consisting of halo, nitro, trifluoromethyl, $(C_1-C_8)$ alkyl, $(C_1-C_8)$ alkoxy, aryl, and $N(R^a)(R^b)$ wherein $R^a$ and $R^b$ are each independently selected from the group consisting of H and $(C_1-C_8)$ alkyl.

$R^5$ is preferably $-CH_2-$, optionally substituted with 1 or 2 substituents selected from the group consisting of halo, nitro, trifluoromethyl, $(C_1-C_8)$ alkyl, $(C_1-C_8)$ alkoxy, aryl, and $N(R^a)(R^b)$ wherein $R^a$ and $R^b$ are each independently selected from the group consisting of H and $(C_1-C_8)$ alkyl.

In one preferred embodiment, each of $R^6$, $R^7$ and $R^8$ is $-CH_3$, each optionally substituted with 1 or 2 substituents selected from the group consisting of halo, nitro, trifluoromethyl, $(C_1-C_8)$ alkyl, $(C_1-C_8)$ alkoxy, aryl, and $N(R^a)(R^b)$ wherein $R^a$ and $R^b$ are each independently selected from the group consisting of H and $(C_1-C_8)$ alkyl.

$X^1$ is preferably S, O or NHC=O.
$X^2$ is preferably S, O or NHC=O.
$X^3$ is preferably O or S.
$E^1$ is preferably $N_3$, S, or H.
$Z^1$ is preferably H.
$E^2$ is preferably $N_3$, S or H.
$Z^2$ is preferably H.

$D^1$ is preferably cytosine, guanine, inosine or thymine, wherein $D_1$ is optionally substituted with 1, 2, 3, or 4 substituents selected from the group consisting of halo, nitro, trifluoromethyl, $(C_1-C_8)$ alkyl, $(C_1-C_8)$ alkoxy, aryl, and $N(R^a)(R^b)$ wherein $R^a$ and $R^b$ are each independently selected from the group consisting of H and $(C_1-C_8)$ alkyl.

$D^2$ is preferably cytosine, guanine, inosine or thymine, wherein $D_2$ is optionally substituted with 1, 2, 3 or 4 substituents selected from the group consisting of halo, nitro, trifluoromethyl, $(C_1-C_8)$ alkyl, $(C_1-C_8)$ alkoxy, aryl, and $N(R^a)(R^b)$ wherein $R^a$ and $R^b$ are each independently selected from the group consisting of H and $(C_1-C_8)$ alkyl.

The invention also includes a compound which exhibits antiviral activity having the chemical structure of Formula II or a pharmaceutically acceptable salt thereof.

Formula II is wherein,
$R^1$ is $(C_6-C_{16})$ alkyl, branched alkyl, alkenyl or alkynyl;
$R^2$ is $(C_4-C_{12})$ alkylene;
$R^3$ is $-CH_2CH_2-$;
$R^5$ is $-CH_2-$;
$R^6$, $R^7$ and $R^8$ are each $CH_3$;
$X^1$ and $X^2$ are each independently S, O or NHC=O;
$E^2$ is H or $N_3$, and
$D^2$ is selected from the group consisting of thymine, cytosine, guanine and inosine.

In Formula II, each alkyl, branched alkyl, alkenyl, alkynyl, thymine, cytosine, guanine, and inosine of $R^1$, $R^2$, $R^3$, $R^5$, $R^6$, $R^7$, $R^8$, and $D^2$ can, optionally, be substituted with 1, 2, 3, or 4 substituents independently selected from the group consisting of halo, nitro, trifluoromethyl, $(C_1-C_8)$ alkyl, $(C_1-C_8)$ alkoxy, aryl, and $N(R^a)(R^b)$, wherein $R^a$ and $R^b$ are each independently selected from the group consisting of H and $(C_1-C_8)$ alkyl.

The present invention also includes compounds which are useful in drug delivery for treating or alleviating a disease or combating a cancer in a mammal. The compounds are also useful for facilitating delivery of a therapeutic agent to a mammalian cell. Accordingly, the invention includes a compound having the chemical structure of Formula III or a pharmaceutically acceptable salt thereof.

Formula III is wherein,
$R^{11}$ is $(C_1-C_{16})$ alkyl, branched alkyl, alkenyl or alkynyl;
$R^{12}$ is $(C_1-C_{16})$ alkyl, branched alkyl, alkenyl or alkynyl;
$X^{11}$ is O, S, or NHC=O;
$X^{12}$ is O, S, or NHC=O;
$X^{13}$ is O or S;
n is 0, 1 or 2, and
$R^{13}$ is a therapeutic agent.

In Formula III, each alkyl, branched alkyl, alkenyl, alkynyl, adenine, thymine, cytosine, guanine, pyrimidine, purine, hypoxanthine, inosine and uracil of $R^{11}$, $R^{12}$, and $R^{13}$ can, optionally, be substituted with 1, 2, 3, or 4 substituents independently selected from the group consisting of halo, nitro, trifluoromethyl, $(C_1-C_8)$ alkyl, $(C_1-C_8)$ alkoxy, aryl, and $N(R^a)(R^b)$ wherein $R^a$ and $R^b$ are each independently selected from the group consisting of H and $(C_1-C_8)$ alkyl.

In Formula III, if n is 1 or 2, the compound is a phospholipase C substrate and is not a phospholipase A substrate. Also, if n is 1 or 2, the compound is converted to an alkyl lipid and a moiety selected from the group consisting of a nucleoside monophosphate and a nucleoside analogue monophosphate intracellularly in a mammal, and is not converted to an alkyl lipid and a moiety selected from the group consisting of a nucleoside monophosphate and a nucleoside analogue monophosphate extracellularly in a mammal.

The conjugate compounds of Formula III can be formulated in pharmaceutical compositions as described herein, which have the advantageous properties of being suitable for oral administration, can be readily absorbed from the gastrointestinal tract, can cross the blood-brain barrier and be of value in the treatment of CNS diseases and cancers. These conjugates can be used in a number of different cell lines including, by way of example and not by limitation, brain tumor cells, lymphoid cells and pancreatic tumor cells.

In compounds of Formula III which have at least one phosphate group (i.e., n=1 or 2) the phosphate ester linkage is cleaved intracellularly in a mammal by the action of a phospholipase C-like activity to release intracellularly a phospholipid and an anticancer agent. These compounds are substrates of phospholipase C, but not substrates of phospholipase A. Because the phospholipase C activity is intracellular, the conjugates are only converted to a phospholipid and a nucleoside monophosphate intracellularly, and not extracellularly. The metabolism of these compounds by an intracellular phospholipase C-like activity enables the compounds to be used in methods which circumvent the rate limiting step for the activation of nucleoside analogue prodrugs, namely, the conversion of nucleoside analogue to nucleoside analog monophosphate. Because they are metabolized intracellularly to release a nucleoside analogue monophosphate, the administration of these compounds results in the ability to provide an anticancer agent which can be effective in cancer cells which lack a kinase enzyme such as, for example, deoxycytidine kinase, as a mechanism of cellular anticancer drug resistance. Additionally, the phospholipid moiety can affect signal transduction pathways involving protein kinase C and MAP kinase signaling cascades.

The released nucleoside monophosphate serves two purposes. First, it bypasses the rate limiting step in the activation of several nucleoside prodrugs, namely, deoxycytidine kinase. Second, the polar phosphate group "locks" the nucleoside within the cell. The phospholipid conjugate also serves as a reservoir for the drug, increasing the drugs half-life. The capacity to conjugate other small molecular weight compounds to the phospholipid backbone for the treatment of other diseases of the central nervous system (i.e. Alzheimer's) is also of great utility. For example, an ether-lipid moiety can be used as a backbone for conjugation to a variety of therapeutic agents including nucleoside analogues, anticancer and antiviral agents, ribozymes and antisense oligonucleotides. Since the ether-lipid backbone is lipophilic, these conjugates can cross the blood-brain barrier and be used as prodrugs in the treatment of CNS diseases, such as Alzheimer's and neurologic degenerative diseases. The lipophilic property of the conjugates enables them to cross the blood-brain barrier, and thus bypass the requirement for an active transport system in the cell in which uptake of the drug is desired.

In preferred compounds of Formula III, $R^{11}$ is a $C_{12}$ alkyl, branched alkyl, alkenyl or alkynyl;

$R^{12}$ is $C_8H_{16}$ alkyl or branched alkyl;

n=1, and $R^{13}$ is an anticancer agent.

Preferably, the anticancer agent is selected from the group consisting of gemcitabine, ara-C, 5-azacytidine, cladribine, fludarabine, fluorodeoxyuridine, cytosine arabinoside 6-mercaptopurine, 6-thioguanine, 5-deoxyfluorouridine, ftorafur, capecitabine, 5-deoxy-5-fluorocytidine, 5-azacytsine arabinoside, troxacitabine, and pentostatin, wherein the phosphorus atom of the phosphate moiety is covalently linked in a phosphate ester linkage to the oxygen atom of the 5' hydroxyl group of a sugar moiety of $R^{13}$.

The invention includes additional compounds which are useful in drug delivery for treating or alleviating a disease or combating a cancer in a mammal. The compounds are also useful for facilitating delivery of a therapeutic agent to a mammalian cell. Accordingly, the invention includes a compound having the chemical structure of Formula IV or a pharmaceutically acceptable salt thereof.

Formula IV is $$\begin{array}{c} H_2C-X^{21}-R^{21} \\ | \\ R^{22}-X^{22}-CH \\ | \\ H_2C-X^{23}\left[\begin{array}{c} O \\ \| \\ P-CH_2 \\ | \\ O^- \end{array}\right]_n R^{23} \end{array} \quad (IV)$$

wherein, $R^{21}$ is ($C_6$ to $C_{16}$) alkyl, branched alkyl, alkenyl, or alkynyl;

$R^{22}$ is ($C_1$ to $C_{12}$) alkyl, branched alkyl, alkenyl, or alkynyl;

$X^{21}$ is O, S, or NHC=O;

$X^{22}$ is O, S, or NHC=O;

$X^{23}$ is O or S;

n is 1 or 2, and $R^{23}$ is a therapeutic agent.

In Formula IV, each alkyl, branched alkyl, alkenyl, alkynyl, adenine, thymine, cytosine, guanine, pyrimidine, purine, hypoxanthine, inosine and uracil of $R^{21}$, $R^{22}$, and $R^{23}$ can, optionally, be substituted with 1, 2, 3, or 4 substituents independently selected from the group consisting of halo, nitro, trifluoromethyl, ($C_1$-$C_8$) alkyl, ($C_1$-$C_8$) alkoxy, aryl, and N($R^a$)($R^b$) wherein $R^a$ and $R^b$ are each independently selected from the group consisting of H and ($C_1$-$C_8$) alkyl.

In preferred compounds of Formula IV, $R^{21}$ is $C_{12}$ alkyl;

$R^{22}$ is $C_{10}$ alkyl;

n=1, and $R^{23}$ is an anticancer agent.

Preferably, the anticancer agent is selected from the group consisting of gemcitabine, ara-C, 5-azacytidine, cladribine, fludarabine, fluorodeoxyuridine, cytosine arabinoside 6-mercaptopurine, 6-thioguanine, 5-deoxyfluorouridine, ftorafur, capecitabine, 5-deoxy-5 -fluorocytidine, 5-azacytsine arabinoside, troxacitabine, and pentostatin, wherein the methylene group of the phosphonate moiety is covalently linked to the oxygen atom of the 5' hydroxyl group of a sugar moiety of $R^{23}$.

The invention includes additional compounds which are useful in drug delivery for treating or alleviating a disease or combating a cancer in a mammal. The compounds are also useful for facilitating delivery of a therapeutic agent to a mammalian cell. Accordingly, the invention includes a compound having the chemical structure of Formula V or a pharmaceutically acceptable salt thereof.

Formula V is

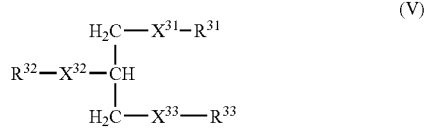

wherein, $R^{31}$ is ($C_1$ to $C_{16}$) alkyl, branched alkyl, alkenyl, or alkynyl;

$R^{32}$ is ($C_1$ to $C_{16}$) alkyl, branched alkyl, alkenyl, or alkynyl;

$X^{31}$ is O, S, or NHC=O;

$X^{32}$ is O, S, or NHC=O;

$X^{33}$ is —OH, —SH, or amino, and $R^{33}$ is a therapeutic agent.

In Formula V, each alkyl, branched alkyl, alkenyl, alkynyl, adenine, thymine, cytosine, guanine, pyrimidine, purine, hypoxanthine, inosine and uracil of $R^{31}$, $R^{32}$, and $R^{33}$ can, optionally, be substituted with 1, 2, 3, or 4 substituents independently selected from the group consisting of halo, nitro, trifluoromethyl, ($C_1$-$C_8$) alkyl, ($C_1$-$C_8$) alkoxy, aryl, and N($R^a$)($R^b$) wherein $R^a$ and $R^b$ are each independently selected from the group consisting of H and ($C_1$-$C_8$) alkyl.

In preferred compounds of Formula V, $R^{31}$ is ($C_6$-$C_{16}$) alkyl branched alkyl alkenyl or alkynyl;

$R^{32}$ is ($C_1$-$C_8$) alkyl, branched alkyl, alkenyl or alkynyl, and $R^{33}$ is an anticancer agent.

Preferably, the anticancer agent is selected from the group consisting of mitoxanthrone, doxorubicin, idarubicin, epirubicin, daunorubicin, mitomycin, methotrexate, CPT-11, SN-38, camptothecin, topotecan, 9-nitrocamptothecin, and 9-aminocamptothecin, and is covalently linked via an ester, amido or carbamate linkage to the —SH, OH or amino group of $X^{33}$.

Compounds of Formula I and Formula II can be prepared according to procedures known to the skilled artisan (See, for example, Marx et al., 1988, Journal of Medicinal Chemistry 31:858-863; Meyer et al., 1991, Journal of Medicinal Chemistry 34:1377-1383; Morris-Natschke et al., 1986, Journal of Medicinal Chemistry 29:2114-2117; Piantadosi et al., 1991, Journal of Medicinal Chemistry 34:1408-1414; and Surles et al., 1993, Lipids 28:55-57).

Figure 2:
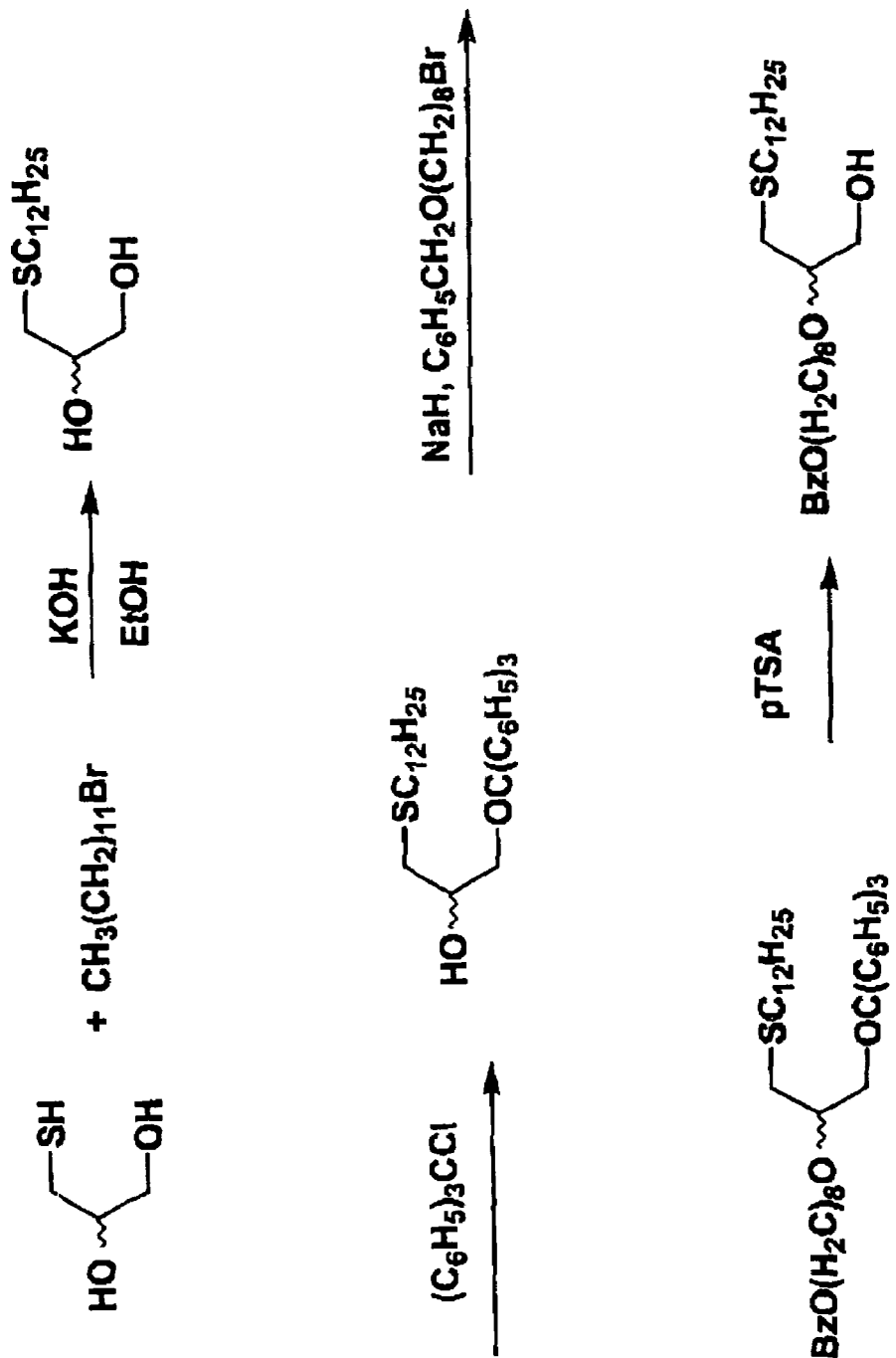
FIG. 2 is a reaction scheme depicting the synthesis method for preparing a lipid backbone (i.e. an alkyl lipid) for the compounds of the invention.
Figure 3:
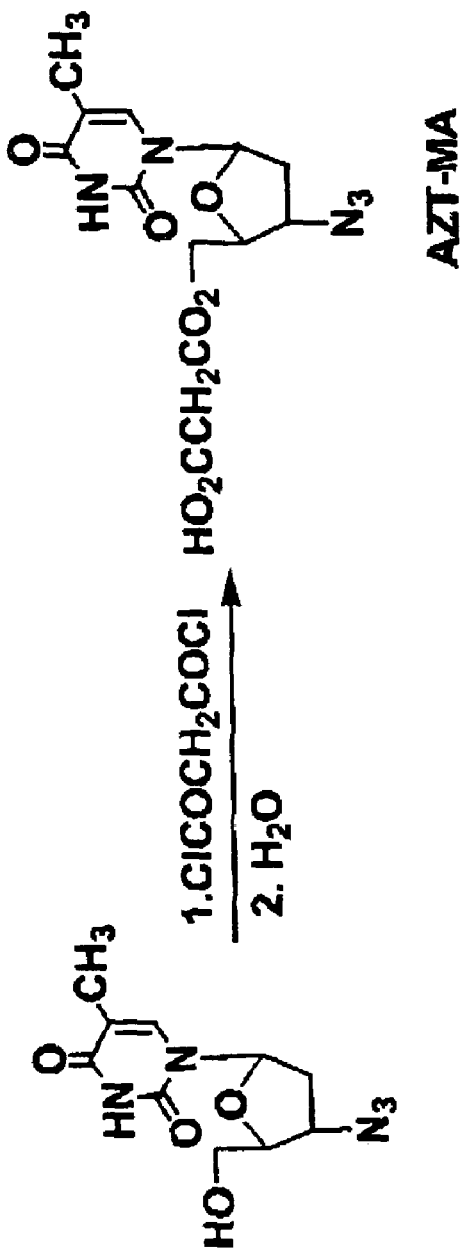
FIG. 3 is a reaction scheme depicting the synthesis method for preparing an AZT-malonic acid (AZT-MA) compound, which is an intermediate compound in the synthesis of the double targeting PC lipid-AZT conjugate compounds of the invention.
Figure 4:
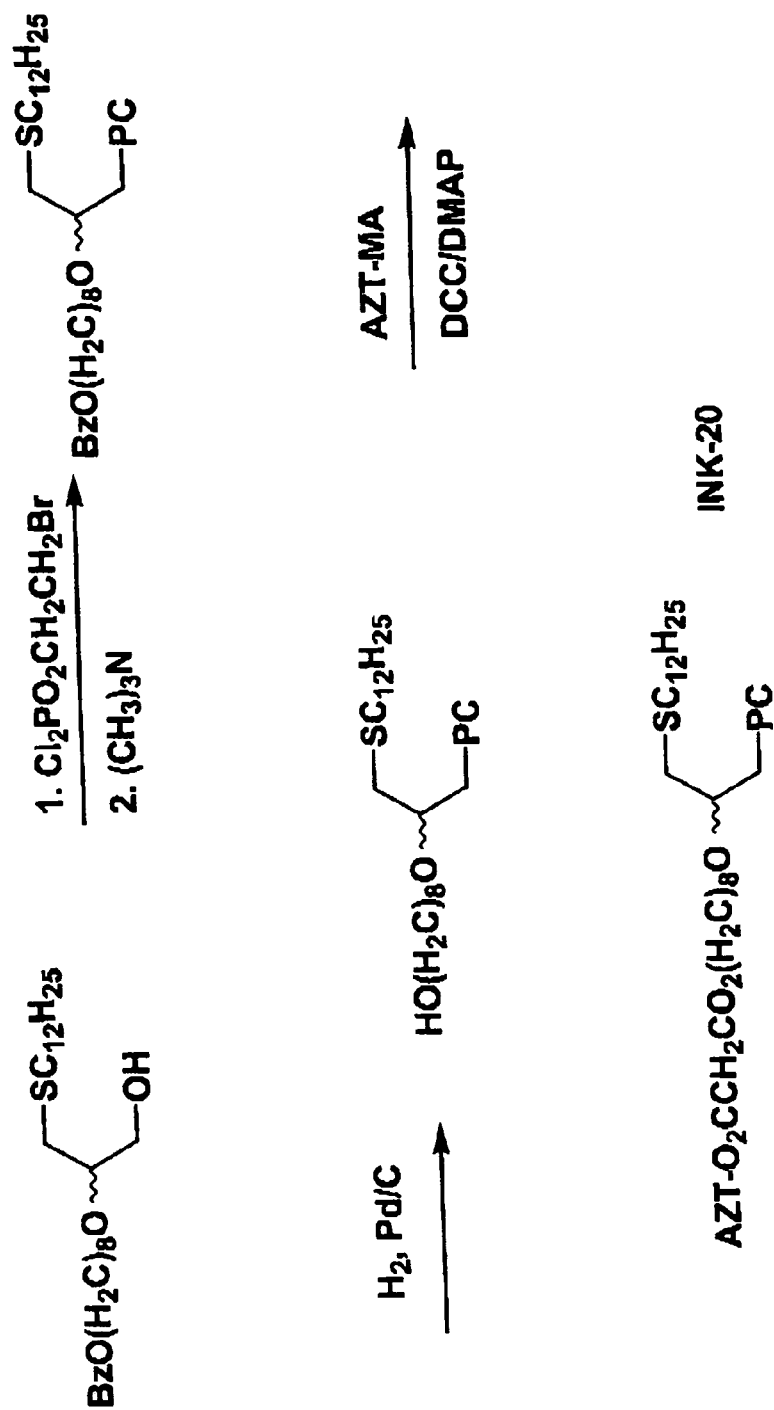
FIG. 4 is a reaction scheme depicting the synthesis method for preparing a double targeting PC lipid-AZT conjugate compound of the invention (INK-20).
Figure 5:
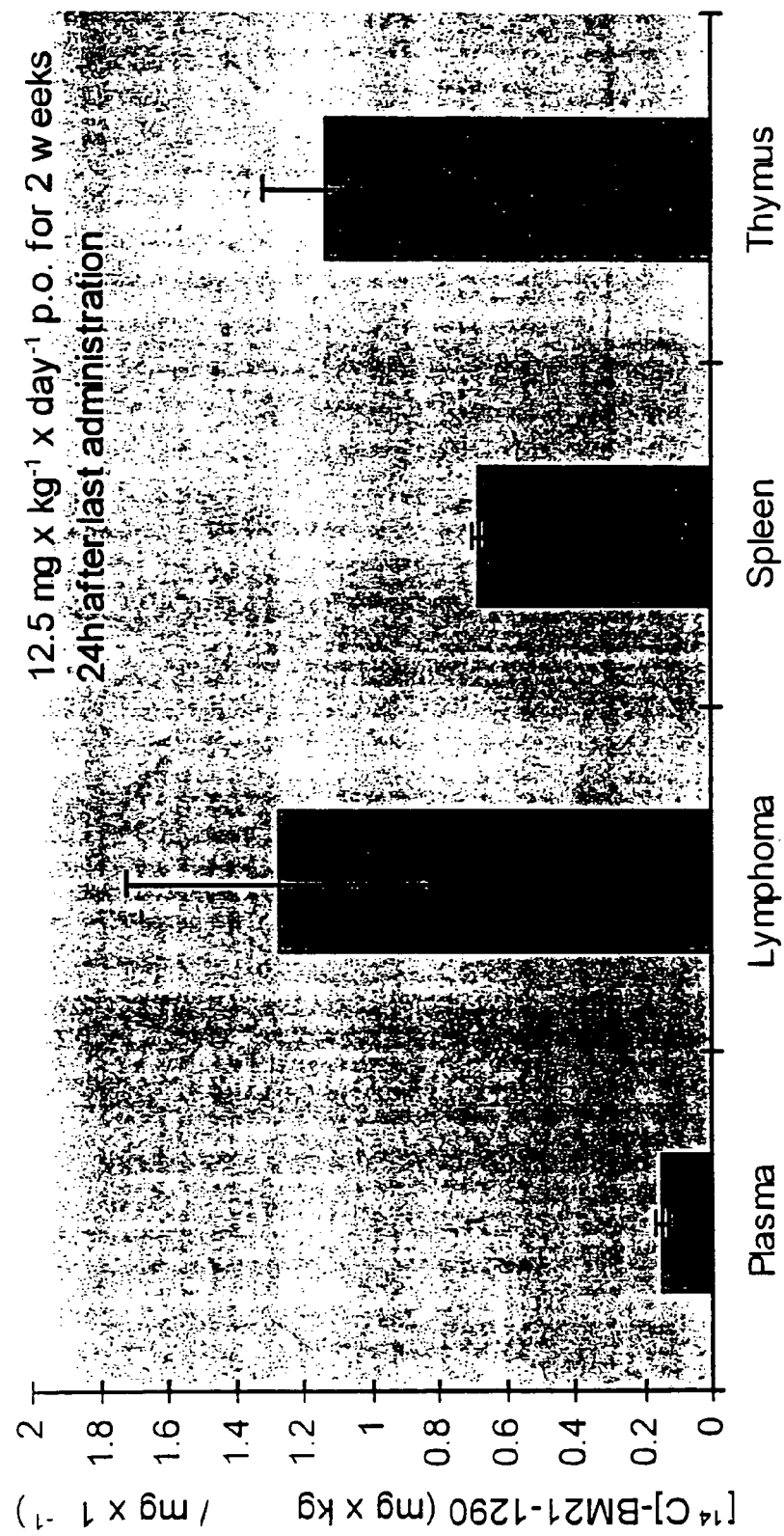
FIG. 5, comprising
Figure 6:
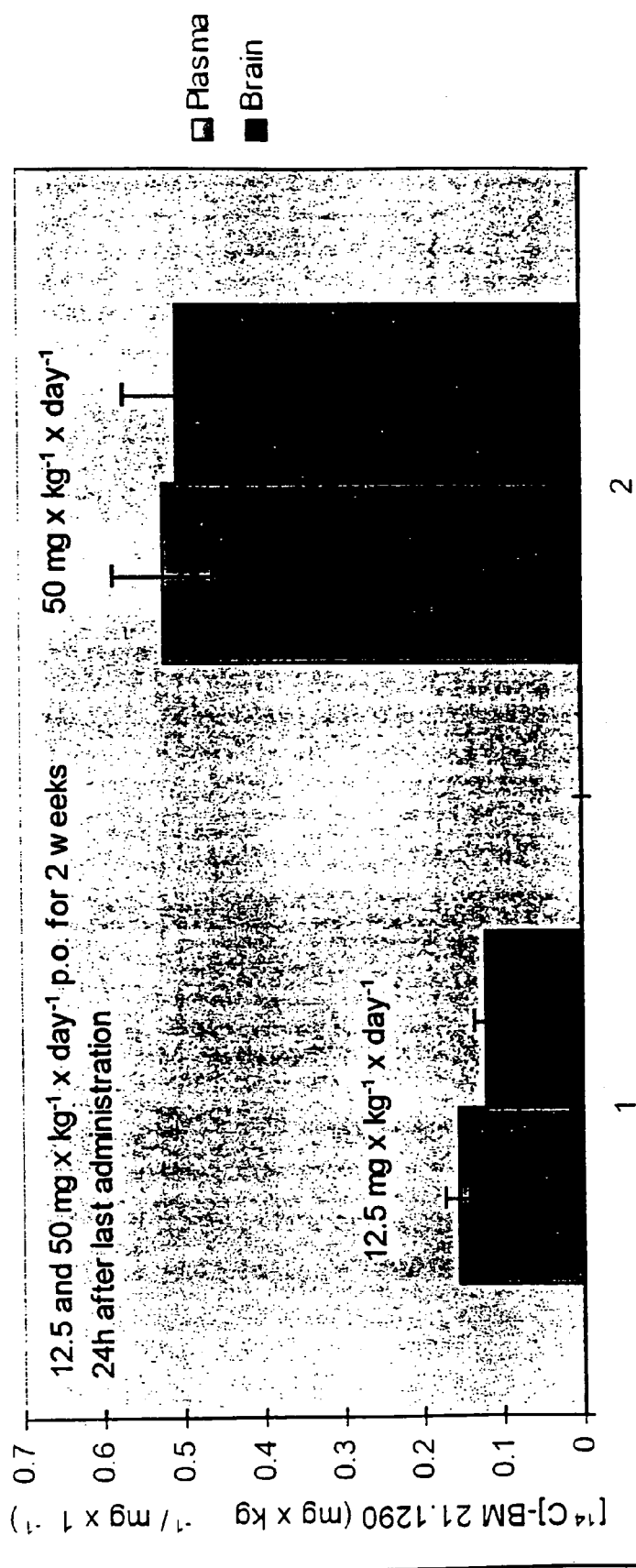
FIG. 6, comprising

An example of such a procedure is illustrated in FIGS. 2-4. The structures presented in the reaction schemes of FIGS. 2-4 are representative and not meant to limit the compounds of the invention. Modifications to the reactions in FIGS. 2-4 using different compounds are apparent to the skilled artisan. Briefly, a compound of Formula I or Formula II is prepared by reacting a lipid backbone moiety, prepared as shown in FIG. 2, for example, with an AZT-malonic acid (AZT-MA) moiety, for example, prepared as shown in FIG. 3. Synthetic methods for the preparation of a lipid backbone as described in FIG. 2 are known in the art. For example, the synthesis method for preparing a lipid backbone for a thiophosphocholine is described in Morris-Natschke et al., 1986, Journal of Medicinal Chemistry 29(10):2114-2117, except one would substitute the benzyloxy alkyl bromide for the C-2 alkyl chain described in the reference. To prepare an amidophosphocholine, for example, one would follow the synthesis method described in Kucera et al., 1998, Antiviral Chemistry and Chemotherapy, 9:157-165. However, one would substitute $C_6H_5CH_2O(CH_2)_8Br$ (8-benzyloxyoctyl bromide) for $CH_3(CH_2)_7Br$ (octyl bromide) described in the reference. To prepare a lipid backbone for various other phosphocholine syntheses, one would follow the synthesis procedures described in Meyer et al., 1991, Journal of Medicinal Chemistry 34(4):1377-1383 and Morris-Natschke et al., 1993, Journal of Medicinal Chemistry 36(14) 2018-2023. Again, one would substitute the benzyloxy alkyl bromide for the C-2 alkyl chain described in the references.

A preferred compound of the invention (e.g. INK-20, a PC lipid-AZT conjugate) can be prepared as described in the Examples herein and depicted in FIG. 4 by reacting the lipid backbone moiety generated as shown in FIG. 2 with the AZT-malonic acid (AZT-MA) moiety generated as shown in FIG. 3. The AZT-MA moiety can be prepared, for example, as described in the Examples herein. FIGS. 2-4 together illustrate the reaction scheme for preparation of certain preferred compounds of the invention, wherein AZT is linked to a PC lipid at the terminal functionality of position-2 on a modified thioglycerol backbone. The intermediate thiophosphocholine in FIG. 4 has a terminal hydroxyl group on the position-2 side chain which is used as a site for conjugating AZT to the PC lipid. An antiviral agent such as, for example, AZT or a protease inhibitor can be linked to the PC lipid via a malonic ester. This synthetic pathway allows manipulation of the rate of esterase-catalyzed hydrolysis of the AZT moiety in the cell by incorporation of substituted malonic linking groups. While not wishing to be bound by any particular theory, it is expected that, as with accepted prodrug strategy, the ester bond linking the PC lipid with the AZT moiety is cleaved by the action of esterase-like activity in vivo, thereby releasing both active antiviral agents (e.g. nucleoside or protease inhibitor and PC lipid) inside treated cells (See Chapter 47, "Chemotherapy of Microbial Agents," pp. 1130 and 1141, respectively, in Goodman and Gilman, 1996, "The Pharmacological Basis of Therapeutics", Ninth Ed.).

The following compounds are illustrative of compounds having structures according to one or both of Formula I and Formula II, as described above. These compounds can be prepared by the procedures described herein, or by variations thereof which are apparent to those skilled in the art in view of the instant disclosure. Exemplary compounds include INK-20, INK-25 and INK-26. The chemical structures of these compounds are depicted in Table 1 herein.

Compounds of Formulae III, IV and V can be prepared according to procedures known to the skilled artisan. An example of such a procedure is described, for example, in Piantadosi et al., 1991, J. Med. Chem. 34:1408-1414. The synthesis of a compound of Formula V involves direct esterification of the lipid portion with the therapeutic agent rather than conjugation of the therapeutic agent with the phosphatidic acid portion of Formulae III and IV.

Figure 7A:
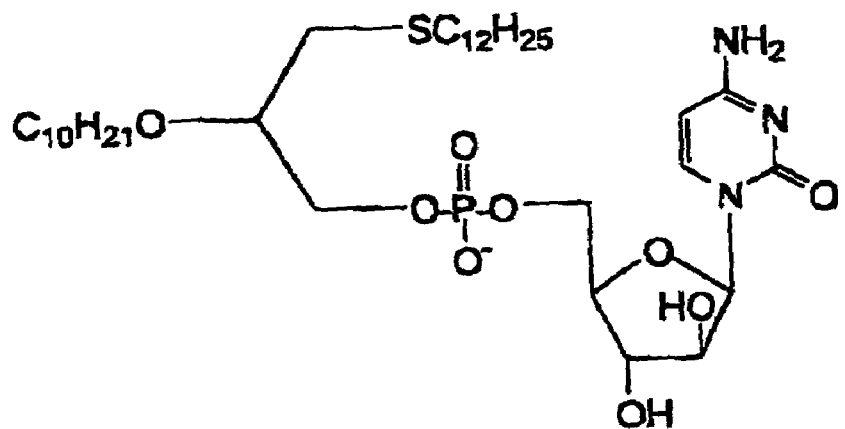
FIG. 7 is a formula depicting the chemical structure of an exemplary compound of Formula V.
Figure 7B:
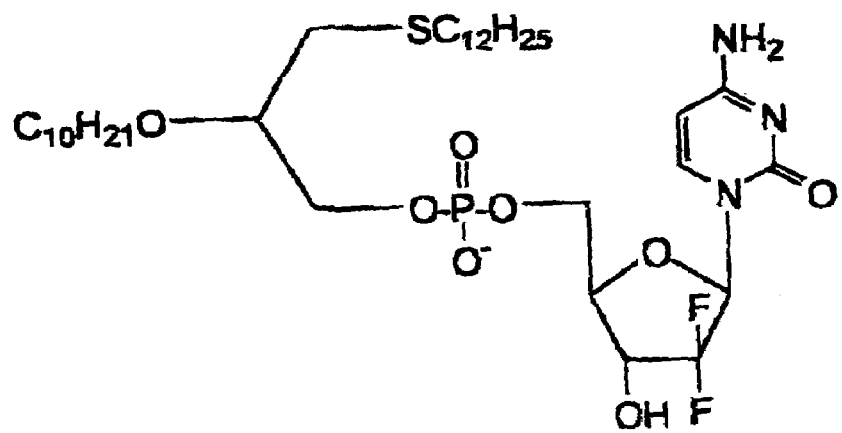
Figure 8A:
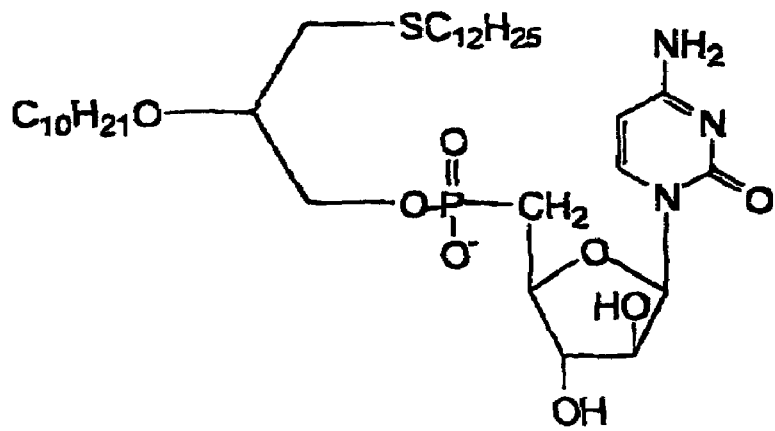
Figure 8B:
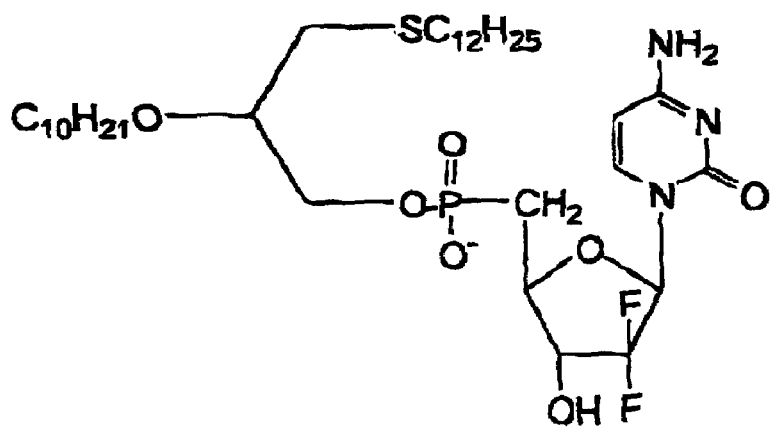
Figure 9:
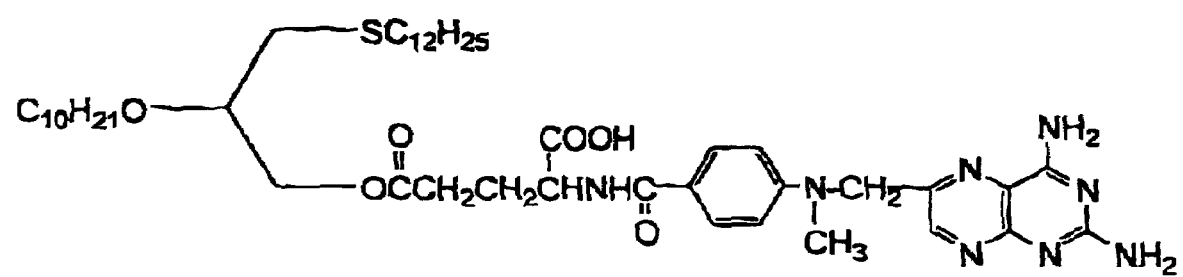

Exemplary compounds having structures according to Formulae III, IV and V, are described herein in the Figures. These compounds can be prepared by the procedures described herein, or by variations thereof which are apparent to those skilled in the art in view of the instant disclosure. Structural formulae of exemplary compounds are shown in FIG. 7 (Formula III), FIG. 8 (Formula IV), and FIG. 9 (Formula V).

The compounds of the present invention can be prepared in the form of a pharmaceutically acceptable salt or a non-pharmaceutically acceptable salt. Non-pharmaceutically acceptable salts are useful, for example, as intermediates for preparation of a pharmaceutically acceptable salt. When the compounds are sufficiently basic or acidic to form stable non-toxic acid or base salts, the compounds may be prepared as a pharmaceutically acceptable salt. Pharmaceutically acceptable salts are salts that retain the desired biological activity of the parent compound and do not impart undesirable toxicological effects.

Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chlorine, bromine, and iodine; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sufate and potassium sulfate; and salts formed from metal nitrates, for example, sodium nitrate and potassium nitrate.

Pharmaceutically acceptable and non-pharmaceutically acceptable salts may be prepared using procedures well known in the art, for example by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made.

The compounds of Formulae I-V can be formulated as pharmaceutical compositions and administered to a mammal, such as a human patient by a chosen route of administration. Pharmaceutical compositions that are useful in the methods of the invention can be prepared, packaged, or sold in a variety of formulations which can be suitable for one or more routes of administration such as, for example, oral, intravenous, intramuscular, topical, subcutaneous, rectal, vaginal, parenteral, pulmonary, intranasal, buccal, ophthalmic, or another route of administration. Other contemplated formulations include projected nanoparticles, liposomal preparations, resealed erythrocytes containing the active ingredient, and immunologically-based formulations.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates and mammals including commercially relevant mammals such as cattle, pigs, horses, sheep, cats, and dogs.

Thus, the present compounds can be systemically administered (e.g. orally) in combination with a pharmaceutically acceptable vehicle such as an inert diluent or an assimilable edible carrier. They can be enclosed in hard or soft shell gelatin capsules, compressed into tablets, or incorporated directly into the food of the patient's diet. For oral therapeutic administration, the active compound can be combined with one or more excipients and used in the form of ingestible tablets, buccal tablets, troches, capsules, elixirs, suspensions, syrups, wafers, and the like. Such compositions and preparations should contain at least 0.1% (w/w) of active compound. The percentage of the compositions and preparations can, of course, be varied, for example from about 0.1% to nearly 100% of the weight of a given unit dosage form. The amount of active compound in such therapeutically useful compositions is such that an effective dosage level will be obtained upon administration.

The tablets, troches, pills, capsules, and the like can also contain one or more of the following: binders such as gum tragacanth, acacia, corn starch, or gelatin; excipients such as dicalcium phosphate; a disintegrating agent such as corn starch, potato starch, alginic acid, and the like; a lubricant such as magnesium stearate; a sweetening agent such as sucrose, fructose, lactose, or aspartame; and a flavoring agent such as peppermint, oil of wintergreen, or cherry flavoring. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, sugar, and the like. A syrup or elixir can contain the active compound, sucrose or fructose as a sweetening agent, methyl and propylparabens as preservatives, a dye, and flavoring such as cherry or orange flavor. Of course, any material used in preparing a unit dosage form should be pharmaceutically acceptable and substantially non-toxic in the amounts employed. In addition, the active compound can be incorporated into sustained-release preparations and devices.

The active compound can be administered intravenously or intraperitoneally by infusion or injection. Solutions of the active compound or its salts can be prepared in water, optionally mixed with a non-toxic surfactant. Dispersions can be prepared in glycerol, liquid polyethylene glycols, triacetin, mixtures thereof, and in oils. Under ordinary conditions of storage and use, these preparations contain a preservative to prevent growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid, and stable under conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by formation of liposomes, by the maintenance of the required particle size (in the case of dispersions) or by use of one or more surfactants. Microbial growth can be prevented using various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be achieved using agents which delay absorption, for example, aluminum monostearate and gelatin.

Sterile injectable solutions are prepared by incorporating the active compound in the required amount in an appropriate solvent, optionally with one or more of the other ingredients enumerated above, followed by filter sterilization. In the case of sterile powders for preparation of sterile injectable solutions, preferred methods of preparation include vacuum drying and the freeze drying techniques, which yield a powder of the active ingredient and any additional desired ingredient present in the previously sterile-filtered solution(s).

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

For topical administration, the present compounds can be applied in pure form, i.e., as a liquid. However, it will generally be desirable to administer the compounds to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols, glycols, and blends of two or more of these, in which the present compounds can be dissolved or dispersed at effective levels, optionally with the aid of non-toxic surfactants. Adjuvants such as fragrances and additional antimicrobial agents can be added to optimize properties for a given use. The resulting liquid compositions can be applied using absorbent pads, used to impregnate bandages or other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Accordingly, the invention includes pharmaceutical compositions comprising one or more compounds of Formula I, Formula II, Formula III, Formula IV or Formula V, or any combination thereof, or a pharmaceutically acceptable salt thereof, in combination with a pharmaceutically acceptable carrier.

In a preferred embodiment, the pharmaceutical composition is adapted for oral, topical, or parenteral administration to a mammal such as a human, and comprises one or more compounds of Formula I or Formula II, or any combination thereof, or a pharmaceutically acceptable salt thereof, in an amount effective to treat a virus infection in a mammal or in a cell, particularly wherein the virus is HIV, hepatitis virus, or herpes simplex virus.

As used herein, "treatment" of a virus infection can mean, for example, any one or more of the following: inhibiting the replication of the virus, reducing the virus load within a patient, inhibiting formation of infectious progeny virus, inhibiting infectiousness of virus, killing cells harboring virus, interfering with one or more stages of the virus life cycle, inhibiting one or more viral enzymes or inducing production of non-infectious virus particles that can activate an immune response against infectious virus (e.g. autovaccination).

In another preferred embodiment, the pharmaceutical composition is adapted for oral, topical, or parenteral administration to a mammal such as a human, and comprises one or more compounds of Formula III, Formula IV or Formula V, or any combination thereof, or a pharmaceutically acceptable salt thereof, in an amount effective to combat a cancer in a mammal and/or to facilitate delivery of a therapeutic agent to a mammalian cell.

Useful dosages of the compounds of Formulae I-V for inclusion in the pharmaceutical compositions of the invention can be determined by comparing in vitro activity and in vivo activity of the compounds in appropriate animal models. Methods for the extrapolation of effective dosages in mice and other animal models to humans are known in the art (see, for example U.S. Pat. No. 4,938,949).

Generally, the concentration of the compound(s) of Formulae I-V in a liquid composition, such as a lotion, will range from about 0.1% to about 95% by weight, preferably from about 0.5% to about 25% by weight. The concentration in a semi-solid or solid composition such as a gel or a powder will range from about 0.1% to 100% by weight, preferably about 0.5% to about 5% by weight. Single doses for intravenous injection, subcutaneous, intramuscular or topical administration, infusion, ingestion or suppository will generally be from about 0.001 to about 5000 mg, and be administered from about 1 to about 3 times daily, to yield levels of about 0.01 to about 500 mg/kg, for adults.

The invention also includes one or more compounds of Formula I or Formula II, or any combination thereof, in an amount effective to inhibit virus replication in a mammal. The compound of course is therefore useful for inhibiting virus replication in a cell or neutralization (i.e. inactivation) of extracellular virus. Additionally, the invention includes one or more pharmaceutically acceptable salts of a compound of Formula I or Formula II, or any combination thereof, wherein the compound is present in an amount effective to inhibit virus replication in a mammal.

As used herein, to inhibit virus replication in a mammal means to reduce the virus load in a mammal to a level which is lower than the level of the virus load in an otherwise identical mammal which was not administered the compound. Preferably, virus load in a mammal is reduced by about 1 to 12 $\log_{10}$ or more relative to an otherwise identical mammal which was not administered the compound. Virus load in a mammal can be assessed by a number of methods known in the art such as, for example, obtaining a tissue or fluid sample from the mammal and assessing the amount of virus or viral components in the mammal contained therein using technology which is either virological, immunological, biochemical or molecular biological in nature and which is well known to the skilled artisan and which are described elsewhere herein. Inhibition of virus replication in a cell is assessed using similar or identical assays as those used to assess virus load in a mammal.

The invention also includes a kit for administering a composition of the invention (e.g. a compound of the invention, a pharmaceutically acceptable salt thereof, or a pharmaceutical composition of the invention) to a mammal for treatment of a virus infection. Preferably, the mammal is a human. The virus infection can be an infection by any one or more of the viruses described herein. The kit comprises the composition of the invention and an instructional material which describes adventitially administering the composition to the mammal by any of the routes of administration described herein. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the composition of the invention in the kit for any one or more of the following: effecting treatment of a virus infection in a mammal or in a cell; alleviation or treatment of the symptoms of a virus infection in the mammal; combating a cancer in a mammal; or for facilitating delivery of an anticancer agent to a mammalian cell. The instructional material of the kit of the invention may, for example, be affixed to a container which contains the composition of the invention or be shipped together with a container which contains the composition. Alternatively, the instructional material may be shipped separately from the container with the intention that the instructional material and the composition be used cooperatively by the recipient.

The invention also includes a kit for inhibition of virus replication in a cell. The kit comprises a composition of the invention, which can be one or more compounds of Formula I or Formula II, or any combination thereof, a pharmaceutically acceptable salt thereof, and a pharmaceutical composition comprising one or more compounds of Formula I or Formula II, or any combination thereof. The kit also includes an instructional material.

As used herein, inhibition of virus replication in a cell means a reduction in virus replication in a cell to a level lower than the level in an otherwise identical cell which was not administered the composition of the invention. Preferably, the reduction in virus replication is by about 90 to about 99.9% relative to the otherwise identical cell which was not administered the composition of the invention. The level of virus replication in a cell and therefore virus load in a mammal that is also being assessed, can be assessed by any one of numerous methods known to the skilled artisan. For example, the level of virus replication in a cell can be assessed by evaluating the number of virus particles or amount of a viral component, such as a viral protein, a viral enzyme, or viral nucleic acid, in the cell or in fluid or debris associated with the cell. The number of infectious virus particles in a cell can be evaluated, for example, in a plaque assay. The level of a viral component such as a viral protein or enzyme in a cell can be evaluated using standard analytical techniques of protein biochemistry, such as, for example, using an activity assay for a viral enzyme, or using Western blotting or quantitative gel electrophoresis for a viral protein. Viral nucleic acid levels in a cell can be evaluated using standard analytical techniques such as Northern blotting and Southern Blotting or quantitation by polymerase chain reaction (PCR).

The invention includes methods for treatment of a virus infection in a mammal. The methods comprise administering to the mammal one or more compounds of Formula I or Formula II, or any combination thereof, or a pharmaceutically acceptable salt thereof, in an amount effective to treat the virus infection. The compound may be administered by any of the methods described herein. Preferably, the mammal is a human. The virus infection may be caused by any type of virus. Preferably, the virus infection results from infection by a virus selected from the group consisting of HIV-1, HIV-2, hepatitis A virus, hepatitis B virus, hepatitis C virus, hepatitis D virus, hepatitis E virus, herpes simplex virus type 1, herpes simplex virus type 2, varicella-zoster virus, cytomegalovirus, Epstein Barr virus, human herpes virus type 6, human herpes virus type 7 and human herpes virus type 8, parainfluenza viruses and respiratory syncytial viruses.

The invention also includes methods of treating a virus infection in a mammal by contacting the virus in vitro, in vivo or ex-vivo with one or more compounds of Formula I or Formula II, or any combination thereof, or a pharmaceutically acceptable salt thereof, in an amount effective to treat the virus infection (e.g. to inhibit virus replication, infectivity, life cycle processes or pathogenesis). Methods for testing the antiviral activity of a compound in vitro are known to the skilled artisan, and are described, for example, in Kucera et al., 1990, AIDS Res. and Human Retrovir. 6:494.

The invention further includes methods of using one or more compounds of Formula I or Formula II, or any combination thereof, or a pharmaceutically acceptable salt thereof, in medical therapy (preferably for use in treating a virus infection) or for the manufacture of a medicament useful for the treatment of a virus infection.

The invention also includes methods of inhibiting virus replication in a cell. The methods comprise administering to the cell one or more compounds of Formula I or Formula II, or any combination thereof, or a pharmaceutically acceptable salt thereof, in an amount effective to inhibit virus replication in the cell. Inhibition of virus replication in a cell, as described herein, means a reduction in virus replication in a cell to a level lower than the level in an otherwise identical cell which was not administered the compound of the invention. Preferably, the reduction in virus replication is by about 90% to about 99.9% relative to the otherwise identical cell which was not administered the compound of the invention.

The level of virus replication in a cell can be assessed by any one of the methods known to the skilled artisan described herein.

The invention also includes one or more compounds of Formula III, Formula IV or Formula V, or any combination thereof, or a pharmaceutically acceptable salt thereof, wherein the compound is present in an amount effective to facilitate delivery of a therapeutic agent to a mammalian cell. Preferably, the therapeutic agent is an anticancer agent as described herein.

In a preferred embodiment, the compound is suspended in a pharmaceutically acceptable carrier and is present in an amount effective to facilitate delivery of an anticancer agent to a mammalian cell.

Preferably, the cell is in a mammal. Also, preferably, the cell is a cell selected from the group consisting of a CNS cell and a lymphoid cell. Preferred CNS cells include an astrocyte and a glial cell.

Additionally, the invention includes one or more compounds of Formula III, Formula IV or Formula V, or any combination thereof, or a pharmaceutically acceptable salt thereof, wherein the compound is present in an amount effective to combat a cancer in a mammal.

Preferably, the cancer is one or more of a carcinoma, a sarcoma, a neuroblastoma, a leukemia, a lymphoma, and a solid tumor.

In a preferred embodiment, the compound is suspended in a pharmaceutically acceptable carrier and is present in an amount effective to combat a cancer in a mammalian cell.

Preferably, the cell is in a mammal. Also, preferably, the cell is a cell selected from the group consisting of a CNS cell and a lymphoid cell. Preferred CNS cells include an astrocyte and a glial cell.

The invention also includes a drug delivery agent comprising a pharmaceutical composition. The pharmaceutical composition comprises one or more compounds of Formula III, Formula IV or Formula V, or any combination thereof, or a pharmaceutically acceptable salt thereof, in an amount effective to facilitate delivery of a therapeutic agent to a mammalian cell. Preferably, the therapeutic agent is an anticancer agent. Preferably, the cell is in a mammal. Also, preferably, the cell is one or more of a CNS cell and a lymphoid cell.

The invention also includes a drug delivery agent comprising a pharmaceutical composition. The pharmaceutical composition comprises one or more compounds of Formula III, Formula IV or Formula V, or any combination thereof, or a pharmaceutically acceptable salt thereof, in an amount effective to combat a cancer in a mammal. Preferably, the cancer is one or more of a carcinoma, a sarcoma, a neuroblastoma, a leukemia, a lymphoma, and a solid tumor.

Additionally, the invention includes a method of facilitating delivery of a therapeutic agent to a cell. Preferably, the therapeutic agent is an anticancer agent. The method comprises administering to the cell a pharmaceutical composition comprising one or more compounds of Formula III, Formula IV or Formula V, or any combination thereof, or a pharmaceutically acceptable salt thereof, in an amount effective to facilitate delivery of the therapeutic agent to the cell. Preferably, the cell is in a mammal. A preferred cell is a cell selected from the group consisting of a CNS cell and a lymphoid cell.

Further, the invention includes a method of combating a cancer in a mammal. The method comprises administering to the mammal a pharmaceutical composition comprising one or more compounds of Formula III, Formula IV or Formula V, or any combination thereof, or a pharmaceutically acceptable salt thereof, in an amount effective to combat a cancer in the mammal. Preferably, the mammal is a human. A preferred cancer is a cancer selected from the group consisting of a carcinoma, a sarcoma, a neuroblastoma, a leukemia, a lymphoma, and a solid tumor.

The invention also includes a method of treating or alleviating a disease in a mammal. The disease can be any disease experienced by a mammal. Preferably, the disease is one or more of a brain disease, a CNS disease, a lymphatic system disease, a reproductive system disease, a cardiovascular disease, a kidney disease and a liver disease. The method comprises administering to the mammal a pharmaceutical composition comprising a compound of the invention, or a pharmaceutically acceptable salt thereof, in an amount effective to facilitate delivery of a therapeutic agent to a cell in the mammal.

The invention also includes a kit for administering a composition of the invention (e.g. a compound of the invention, a pharmaceutically acceptable salt thereof, or a pharmaceutical composition of the invention) to a mammal for combating a cancer in a mammal. Preferably, the mammal is a human. The cancer can be any of the types of cancer described herein. The kit comprises the composition of the invention and an instructional material which describes adventitially administering the composition to the mammal by any of the routes of administration described herein. In another embodiment, this kit comprises a (preferably sterile) solvent suitable for dissolving or suspending the composition of the invention prior to administering the compound to the mammal.

The invention also includes a kit for facilitating delivery of a therapeutic agent to a mammalian cell. Preferably, the therapeutic agent is an anticancer agent. The kit comprises a composition of the invention, which can be one or more compounds of Formula III, Formula IV or Formula V, or any combination thereof, a pharmaceutically acceptable salt thereof, and a pharmaceutical composition comprising one or more compounds of Formula III, Formula IV or Formula V, or any combination thereof. The kit also includes an instructional material.

The invention is now described with reference to the following Examples. These Examples are provided for the purpose of illustration only and the invention is not limited to these Examples, but rather includes all variations which are evident as a result of the teaching provided herein.

EXAMPLE 1

Anti-HIV-1 Activity of Double-Targeting PC Lipid-AZT Conjugate Compounds

The inhibitory effects of PC lipids, non-PC lipid-AZT conjugates, and double-targeting PC lipid-AZT conjugate compounds of the invention on replication of HIV-1 virus in cells was examined using the plaque assay procedure described in Kucera et al. (1990, AIDS Research and Human Retroviruses, 6:491). CEM-SS cells were seeded at 50,000 cells per milliliter in RPMI growth medium as a monolayer in 96-well dishes, inoculated with 50 to 100 plaque forming units of HIV-1 and overlaid with serial dilutions of either PC lipid, non-PC lipid-AZT conjugate, or PC-lipid-AZT conjugate in RPMI-1640 growth medium supplemented with 10% fetal bovine serum. The structures of the tested compounds are described in Table 1. AZT and PC lipids were used as positive controls. Plaques were counted after incubating the dishes for five days at 37° C. to determine the 50% effective concentration ($EC_{50}$) for the compounds tested. The cytotoxicity of PC lipids, non-PC lipid-AZT conjugates and double targeting PC lipid-AZT conjugates was assessed using the procedure described in Kucera et al. (1990, AIDS Res. And Human Retrovir., 6:496, and 1998, Antiviral Chemistry and Chemotherapy, 9:160).

TABLE 1

(Formula VI)

$$E(CH_2)_qO-\overset{SC_{12}H_{25}}{\underset{OPO_3^-CH_2CH_2\overset{+}{N}(CH_3)_3}{<}}$$

| Compound | Value of "q" in Formula VI | Identity of "E" in Formula VI |
|---|---|---|
| INK 17 | 8 | —OCH$_2$C$_6$H$_5$ |
| INK-18 | 8 | —OH |
| INK-19 | | See structure below |
| INK-20 | 8 | —O$_2$CCH$_2$CO$_2$AZT |
| INK-21 | 10 | —OCH$_2$C$_6$H$_5$ |
| INK-22 | 10 | —OH |
| INK-23 | 12 | —OCH$_2$C$_6$H$_5$ |
| INK-24 | 12 | —OH |
| INK-25 | 10 | —O$_2$CCH$_2$CO$_2$AZT |
| INK-26 | 12 | —O$_2$CCH$_2$CO$_2$AZT |

The structure of INK-19 is

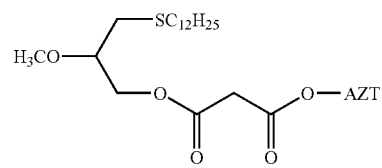

The structure of INK-20 is

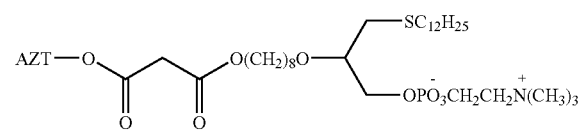

In the plaque assay, HIV-1 syncytial plaques are seen as large, multicellular foci (10 to 25 nuclei/syncytium) that appear either brown and granular or clear. Because the number of HIV-1 syncytial plaques was correlated with reverse transcriptase (RT) and p24 core antigen activity in the HIV-1 infected cell overlay fluids, the syncytial plaque assay could be used to quantify the amount of infectious virus. Reverse transcriptase activity was assayed according to the procedure described by Poeisz et al. (1980, Proc. Natl. Acad. Sci. U.S.A. 77:7415). The activity of p24 core antigen induced by HIV-1 infection of CEM-SS cells was measured spectrophotometrically using the commercial Coulter enzyme immunoassay (EIA).

The results of these assays are presented in Table 2. These results demonstrate that the double-targeting PC lipid-AZT conjugate compounds of the invention exhibit a higher differential selectivity (DS=ratio of $TC_{50}$ for cytotoxicity to $EC_{50}$ for anti-HIV activity) than the PC lipids, the non-PC lipid-AZT conjugates and the positive control, AZT. For example, the compound INK-20 exhibited the highest differential selectivity (DS=7,666) and anti-HIV-1 activity (0.0009 micromolar) of all the compounds tested, while exhibiting a cytotoxicity (6.9±0.6 micromolar) comparable to AZT. The anti-HIV-1 activity of INK-20 was more than ten-fold higher than AZT.

TABLE 2

| Compound | Cytotoxicity ($TC_{50}$) (μM) | Anti-HIV-1 Activity ($EC_{50}$) (μM) | Differential Selectivity |
| --- | --- | --- | --- |
| INK-17[a] | 49.1 ± 13.2 | 0.15 ± 0.13 | 327 |
| INK-18[a] | 50.0 ± 42 | 1.92 ± 1.8 | 26 |
| INK-19[b] | 6.3 ± 1.1 | 0.006 ± 0.001 | 1050 |
| INK-20[c] | 6.9 ± 0.6 | 0.0009 ± 0.00007 | 7666 |
| INK-21[a] | 57.3 ± 10.8 | 1.50 ± 0.23 | 38 |
| INK-22[a] | >90.5 ± 13.4 | 0.39 ± 0.31 | >232 |
| INK-23[a] | >100.0 ± 0.0 | >1.46 ± 0.76 | >68 |
| INK-24[a] | 80.6 ± 6.2 | 0.39 ± 0.39 | 207 |
| INK-25[c] | 13.6 | 0.02 ± 0.01 | 682 |
| INK-26[c] | 11.6 | 0.02 ± 0.02 | 580 |
| BM21-1290[d] | 38.5 | 0.02 | 1925 |
| AZT | 3.7 | 0.009 | 411 |

[a]PC-Lipid
[b]Lipid ester linked-AZT (non-PC lipid-AZT conjugate)
[c]A double-targeting compound of the invention (PC lipid-AZT conjugate)
[d]A thioetherglycerolphospholipid-AZT conjugate (non-PC lipid-AZT conjugate) with AZT at position-3

Data indicating that PC lipids alone can inhibit infectious HIV-1 production, but not reverse transcriptase activity, in acutely infected human lymphocytes (CEM-SS) after 13 days treatment was previously published (Kucera et al., 1990, AIDS Research and Human Retroviruses, 6:497, Table 3). In contrast, the PC lipid-AZT conjugate compounds of the invention can inhibit both infectious HIV-1 production and reverse transcriptase activity in acutely infected human lymphocytes under similar test conditions. In summary, these data support the hypothesis that the PC lipid-AZT conjugate compounds of the invention inhibit both infectious virus production and reverse transcriptase activity.

EXAMPLE 2

Sensitivity of AZT-Resistant Human Clinical Isolates of HIV-1 to PC Lipids Alone and Double Targeting PC Lipid-AZT Conjugate Compounds Sensitivity of AZT-resistant clinical isolates of HIV-1 to PC lipid alone (INK-17 and INK-18), non-PC lipid-AZT conjugate (INK-19) and a double-targeting PC lipid-AZT conjugate compound of the invention (INK-20) was evaluated in matched pairs of clinical isolates of HIV-1 obtained before ("pre-AZT") and after ("post-AZT") administration of AZT to HIV-1 infected humans. Isolates of HIV-1 obtained following administration of AZT included AZT-resistant virus particles. Evaluation of the clinical isolates to the compounds was performed using the plaque assay procedure described herein in Example 1. The matched pairs of clinical isolates were obtained through the AIDS Research and Reference Reagent Program, NIH, Bethesda, Md. The results of these assays are presented in Table 3. The data demonstrate that the double-targeting compound of the invention (INK-20) exhibited a much lower-fold increase in AZT-resistance among HIV-1 clinical isolates than did AZT alone (about 20-fold versus about 680- to 1,100-fold for AZT).

TABLE 3

| | $EC50$ (μM)[a] | | | $EC50$ (μM)[a] | | |
| --- | --- | --- | --- | --- | --- | --- |
| Compound | Pre-AZT G-762 | Post-AZT G-691 | Fold-Increase | Pre-AZT H112-2 | Post-AZT G-910 | Fold-Increase |
| INK-17 | 0.26 | 0.18 | 0 | 0.04 | 0.20 | 5.1 |
| INK-18 | >1.06 | 0.60 | 0 | 0.56 | 1.04 | 1.8 |
| INK-19 | 0.12 | 1.62 | 13.5 | 0.03 | >1.7 | >55.6 |
| INK-20 | 0.04 | 0.74 | 18.6 | 0.02 | 0.44 | 22.0 |
| AZT | 0.001 | >1.29 | >1.170 | 0.002 | >1.36 | >681.7 |

[a]$EC_{50}$ values represent mean values calculated from 2 to 4 independent tests using duplicate wells for each of 4 serial concentrations of compound per test. ">" indicates that $EC_{50}$ was not achieved at the highest concentration tested.
Note
designations such as G-762 and H112-2 in the table designate patient codes for the source of the isolates.

EXAMPLE 3

Anti-Herpes Simplex Virus Type 2 Activity of Double-Targeting PC Lipid-AZT Conjugate Compounds Proof-of-concept of the antiviral activity of the double-targeting PC lipid-AZT conjugate compounds of the invention with respect to herpes simplex virus type 2 was evaluated and compared with that of PC lipid alone and with acyclovir (positive controls). Serial dilutions of PC lipid, PC lipid-AZT conjugate compound, or acyclovir were evaluated for inhibition of the formation of herpes simplex virus type 2 plaques in Vero cells and $EC_{50}$ values were calculated from the results obtained. Briefly, the tests for anti-herpes simplex virus (HSV) activity and cytotoxicity of the compounds were performed by seeding $8\times10^4$ monkey kidney cells (Vero) per ml of D-MEM with 10% fetal bovine serum (FBS) in each well of a 12-well dish. The cultures were incubated at 37° C. to form a complete monolayer. To measure anti-HSV activity and effective concentration $_{50}$ ($EC_{50}$) each cell monolayer was infected with HSV diluted in PBS-A containing about 100 plaque forming units (PFU) per 0.1 ml. After virus attachment (1 hr., 37° C.) the infected monolayers were overlaid with E-MEM containing 2% FBS and 0.5% methyl cellulose with or without added serial concentrations of test compound. After 2 days at 37° C. to allow HSV induced plaque formation, the overlay medium was aspirated, the cell monolayers were fixed with 95% ethanol, stained with 0.1% crystal violet in 20% methanol and distilled water and the number of PFU in the compound treated cultures was divided by the number of PFU in the untreated controls to determine the percent inhibition of PFU. The $EC_{50}$ values were calculated using a computer generated program.

To measure cytotoxicity of the compounds, the cell monolayers (described above) were treated with a serial concentration of test compound for 48 hours at 37° C. and visually examined after crystal violet staining by light microscopy for changes in cell morphology (cell rounding, shrinking, detachment) compared to an untreated control culture. The cytotoxicity (TC$_{50}$) represents the lowest serial concentration of test compound that caused a detectable change in cell morphology in at least 25% of the cells.

The results of these experiments are presented in Table 4. These results indicate that PC lipid-AZT conjugate compounds of the invention are metabolized intracellularly to release two drugs which can target the virus life cycle. The PC lipid compound INK-24 and the AZT conjugate corresponding to INK-24 (i.e. INK-26) both exhibit selective activity against herpes simplex virus type 2, exhibiting EC$_{50}$ values of 13.8 and 12.0 micromolar, respectively. By comparison, the range of EC$_{50}$ values for acyclovir were 12.5, 14.5 and 6.67 micromolar in replicate tests. Because herpes simplex virus is not expected to be inhibited by AZT, the observed inhibition of the virus by INK-26 is most likely due to intracellular metabolism of INK-26, leading to release of biologically active PC lipid. PC lipid should exhibit activity against the herpes simplex virus in a manner and to a degree similar to the anti-herpes virus activity of INK-24. Cytotoxicity attributable to the double-targeting compound INK-26 appeared to be no worse than that of the positive control (acyclovir) and the PC lipid compound INK-24.

TABLE 4

| Compound | Cytotoxicity (TC$_{50}$) (μM) | Anti-Herpes Simplex Activity (EC$_{50}$)[a] (μM) |
| --- | --- | --- |
| INK-17 | toxic @ 4 | >4 |
| INK-18 | ND | ND |
| INK-19 | >20 | >20 |
| INK-20 | toxic @ 20 | >20 |
| INK-21 | toxic @ 20 | >20 |
| INK-22 | toxic @ 20 | >20 |
| INK-23 | >20 | >20 |
| INK-24 | >20 | 13.9, 13.8 |
| INK-25 | toxic @ 20 | >20 |
| INK-26 | >20 | 12.0 |
| Acyclovir control | >20 | 14.5, 12.5, 6.67 |

[a]EC$_{50}$ values represent mean values obtained from 2 independent tests using duplicate wells for each of four serial concentrations of compound per test. ">" indicates that cytotoxicity or EC$_{50}$ was not achieved at the highest concentration tested.

EXAMPLE 4

Synthesis of AZT-Malonic Acid

One gram of AZT was dissolved in 30 ml of anhydrous acetonitrile and added dropwise to a solution of 632 mg of malonyl chloride in 20 ml of acetonitrile at 0° C. The reaction mixture was stirred for 2 hours at 0° C. then at 8-10° C. for 4.5 hours. Thin layer chromatography was used to indicate that the reaction was complete. Water (4 ml) was added. Solvents were removed in vacuo and the residue purified by silica gel chromatography eluting with CHCl$_3$: MeOH. Pure product was obtained in a 68% yield.

EXAMPLE 5

Synthesis of INK-20

The conditions for the first reaction of the synthesis method for INK-20 is described in Kucera et al., 1998, Antiviral Chemistry & Chemotherapy, 9: 157-165 at p. 159 as the two-step synthesis of 3-dodecanamido-2-octyloxypropyl 2-bromethyl phosphate then 3-dodecanamido-2-octyloxypropyl phosphocholine (INK-3). However, the lipid used was 3-dodecylthio-2-(8'-benzyloxyoctyloxy)-1-propanol (see FIG. 4) rather than 3-dodecanamido-2-octyloxy-1-propanol as described in the reference. The reactions were the same. Hydrogenation with H$_2$-Pd/C was performed as follows. The phosphocholine [3-dodecylthio-2-(8'-benzyloxyoctyloxy)propyl phosphocholine] was dissolved in 60 ml absolute EtOH and added to 109 mg of palladium black. This reaction mixture was shaken under 59 psi hydrogen gas for 24 hours. The catalyst was removed by filtration through Celite, solvent was removed in vacuo, and the residue was chromatographed on silica gel using CHCl$_3$:MeOH (100:0 to 2:1) as eluent to give 228 mg (43% yield) of [3-dodeceylthio-2-(8'-hydroxyoctyloxy)propyl phosphophocholine]. AZT-MA (AZT-malonic acid) was then added by the following procedure: One gram of lipid, 192 mg of AZT-MA, 144 mg of dicyclohexylcarbodiimide (DCC), and 9 mg of dimethylaminopyridine (DMAP) were added to 10 ml of DMF. This reaction mixture was stirred at room temperature for 42 hours; copious solid appeared after 18 hours of stirring. The solid was filtered and the solvent removed in vacuo. The residue was chromatographed on silica gel using EtOAc:CHCl$_3$:MeOH (2:2:1) as eluent then CHCl$_3$:MeOH (4:1 to 2:1) to give 141 mg (36% yield) of INK-20 (Rf~0.3 in CHCl$_3$:MeOH:NH$_4$OH 75:25:5).

The disclosures of each and every patent, patent application, and publication cited herein are hereby incorporated herein by reference in their entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A compound having the structure of Formula III:

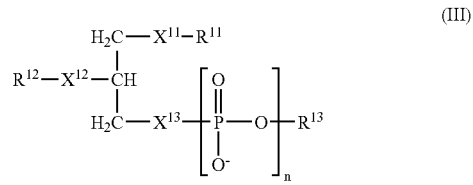

(III)

wherein,
$R^{11}$ is (C$_1$-C$_{16}$) alkyl, branched alkyl, alkenyl or alkynyl;
$R^{12}$ is (C$_1$-C$_{16}$) alkyl, branched alkyl, alkenyl or alkynyl;
$X^{11}$ is O, S, or NHC=O;
$X^{12}$ is O, S, or NHC=O;
$X^{13}$ is O or S;
n is 0, 1 or 2, and
$R^{13}$ is an anticancer agent,
wherein, each and alkynyl of $R^{11}$, $R^{12}$, and $R^{13}$ is, optionally, substituted with 1, 2, 3, or 4 substituents independently selected from the group consisting of halo, nitro, trifluoromethyl, (C$_1$-C$_8$) alkyl, (C$_1$-C$_8$) alkoxy, aryl, and N(R$^a$)(R$^b$) wherein R$^a$ and R$^b$ are each independently selected from the group consisting of H and (C$_1$-C$_8$) alkyl, and
wherein, if n is 1 or 2, the compound is a phospholipase C substrate and is not a phospholipase A substrate, and further wherein, if n is 1 or 2, the compound is converted to an alkyl lipid and a moiety selected from the group consisting of a nucleoside monophosphate and a nucleoside analogue monophosphate intracellularly in a mammal, and is not converted to an alkyl lipid and a moiety selected from the group consisting of a nucleoside monophosphate and a nucleoside analogue monophosphate extracellularly in a mammal.

2. The compound of claim 1,
wherein,
$R^{11}$ is a $C_{12}$ alkyl, branched alkyl, alkenyl or alkynyl;
$R^{12}$ is $C_8H_{16}$ alkyl or branched alkyl;
n=1,
and $R^{13}$ is an anticancer agent selected from the group consisting of gemcitabine, 5-azacytidine, cladribine, fludarabine, fluorodeoxyuridine, cytosine arabinoside and 6-mercaptopurine, wherein the phosphorus atom of the phosphate moiety is covalently linked in a phosphate ester linkage to the oxygen atom of the 5' hydroxyl group of a sugar moiety of $R^{13}$.

3. A compound having the structure of Formula IV:

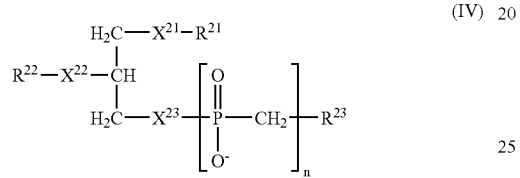

(IV)

wherein,
$R^{21}$ is ($C_6$ to $C_{16}$) alkyl, branched alkyl, alkenyl, or alkynyl;
$R^{22}$ is ($C_1$ to $C_{12}$) alkyl, branched alkyl, alkenyl, or alkynyl;
$X^{21}$ is O, S, or NHC=O;
$X^{22}$ is O, S, or NHC=O;
$X^{23}$ is O or S;
n is 1 or 2;
$R^{23}$ is an anticancer agent, and
wherein, each and alkynyl of $R^{21}$, $R^{22}$, and $R^{23}$ is, optionally, substituted with 1, 2, 3, or 4 substituents independently selected from the group consisting of halo, nitro, trifluoromethyl, ($C_1$-$C_8$) alkyl, ($C_1$-$C_8$) alkoxy, aryl, and $N(R^a)(R^b)$ wherein $R^a$ and $R^b$ are each independently selected from the group consisting of H and ($C_1$-$C_8$) alkyl.

4. The compound of claim 3,
wherein,
$R^{21}$ is $C_{12}$ alkyl;
$R^{22}$ is $C_{10}$ alkyl;
n=1, and
$R^{23}$ is an anticancer agent selected from the group consisting of gemcitabine, 5-azacytidine, cladribine, fludarabine, fluorodeoxyuridine, cytosine arabinoside and 6-mercaptopurine, wherein the methylene group of the phosphonate moiety is covalently linked to the oxygen atom of the 5' hydroxyl group of a sugar moiety of $R^{23}$.

5. A compound having the structure of Formula V:

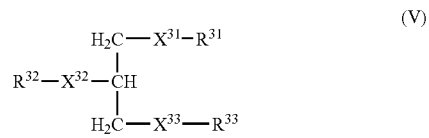

(V)

wherein,
$R^{31}$ is ($C_1$ to $C_{16}$) alkyl, branched alkyl, alkenyl, or alkynyl;

$R^{32}$ is ($C_1$ to $C_{16}$) alkyl, branched alkyl, alkenyl, or alkynyl;
$X^{31}$ is O, S, or NHC=O;
$X^{32}$ is O, S, or NHC=O;
$X^{33}$ is —O, S or amino;
$R^{33}$ is an anticancer agent, and
wherein, each and alkynyl of $R^{31}$, $R^{32}$, and $R^{33}$ is, optionally, substituted with 1, 2, 3, or 4 substituents independently selected from the group consisting of halo, nitro, trifluoromethyl, ($C_1$-$C_8$) alkyl, ($C_1$-$C_8$) alkoxy, aryl, and $N(R^a)(R^b)$ wherein $R^a$ and $R^b$ are each independently selected from the group consisting of H and ($C_1$-$C_8$) alkyl.

6. The compound of claim 5,
wherein,
$R^{31}$ is ($C_6$-$C_{16}$) alkyl, branched alkyl, alkenyl or alkynyl;
$R^{32}$ is ($C_1$-$C_8$) alkyl, branched alkyl, alkenyl or alkynyl, and
$R^{33}$ is an anticancer agent selected from the group consisting of mitoxanthrone, methotrexate and CPT-11, and is covalently linked via an ester, amido or carbamate linkage to the —SH, OH or amino group of $X^{33}$.

7. The compound of claim 1, wherein said compound is suspended in a pharmaceutically acceptable carrier and is present in an amount effective to combat a cancer in a mammal.

8. The compound of claim 7, wherein said cancer is a cancer selected from the group consisting of a carcinoma, a sarcoma, a neuroblastoma, a leukemia, a lymphoma and a solid tumor.

9. The compound of claim 1, wherein said compound is present in an amount effective to facilitate delivery of a therapeutic agent to a mammalian cell.

10. The compound of claim 9, wherein the cell is in a mammal.

11. The compound of claim 10, wherein the cell is a cell selected from the group consisting of a CNS cell and a lymphoid cell.

12. The compound of claim 11, wherein the CNS cell is an astrocyte or a glial cell.

13. A pharmaceutically acceptable salt of the compound of claim 1.

14. The pharmaceutically acceptable salt of claim 13, wherein the compound is present in an amount effective to facilitate delivery of an anticancer agent to a mammalian cell.

15. The pharmaceutically acceptable salt of claim 14, wherein the cell is in a mammal.

16. The pharmaceutically acceptable salt of claim 15, wherein the cell is a cell selected from the group consisting of a CNS cell and a lymphoid cell.

17. The pharmaceutically acceptable salt of claim 13, wherein said compound is present in an amount effective to combat a cancer in a mammal.

18. A pharmaceutically acceptable salt of the compound of claim 2.

19. The pharmaceutically acceptable salt of claim 18, wherein said compound is present in an amount effective to facilitate delivery of an anticancer agent to a mammalian cell.

20. The pharmaceutically acceptable salt of claim 19, wherein said cell is in a mammal.

21. The pharmaceutically acceptable salt of claim 19, wherein said cell is a cell selected from the group consisting of a CNS cell and a lymphoid cell.

22. The pharmaceutically acceptable salt of claim 13, wherein said compound is present in an amount effective to combat a cancer in a mammal.

23. A drug delivery agent comprising a pharmaceutical composition, said composition comprising a compound of claim 1 or a pharmaceutically acceptable salt thereof, in an amount effective to facilitate delivery of an anticancer agent to a mammalian cell.

24. The drug delivery agent of claim 23, wherein said cell is in a mammal.

25. The drug delivery agent of claim 23, wherein said cell is a cell selected from the group consisting of a CNS cell and a lymphoid cell.

26. A drug delivery agent comprising a pharmaceutical composition, said composition comprising a compound of claim 1 or a pharmaceutically acceptable salt thereof, in an amount effective to combat a cancer in a mammal.

27. The drug delivery agent of claim 26, wherein said cancer is a cancer selected from the group consisting of a carcinoma, a sarcoma, a neuroblastoma, a leukemia, a lymphoma and a solid tumor.

28. A drug delivery agent comprising a pharmaceutical composition, the composition comprising a compound of claim 2 or a pharmaceutically acceptable salt thereof, in an amount effective to facilitate delivery of an anticancer agent to a mammalian cell.

29. The drug delivery agent of claim 28, wherein the cell is in a mammal.

30. The drug delivery agent of claim 28, wherein said cell is a cell selected from the group consisting of a CNS cell and a lymphoid cell.

31. A drug delivery agent comprising a pharmaceutical composition, said composition comprising a compound of claim 2 or a pharmaceutically acceptable salt thereof, in an amount effective to combat a cancer in a mammal.

32. The drug delivery agent of claim 31, wherein said cancer is a cancer selected from the group consisting of a carcinoma, a sarcoma, a neuroblastoma, a leukemia, a lymphoma and a solid tumor.

33. A method of facilitating delivery of an anticancer agent to a mammalian cell, said method comprising administering to said cell a pharmaceutical composition comprising a compound of claim 1 or a pharmaceutically acceptable salt thereof, in an amount effective to facilitate delivery of said anticancer agent to said cell.

34. The method of claim 33, wherein said cell is in a mammal.

35. The method of claim 33, wherein the cell is a cell selected from the group consisting of a CNS cell and a lymphoid cell.

36. A method of facilitating delivery of an anticancer agent to a cell, said method comprising administering to said cell a pharmaceutical composition comprising a compound of claim 2 or a pharmaceutically acceptable salt thereof, in an amount effective to facilitate delivery of said anticancer agent to said cell.

37. The method of claim 36, wherein said cell is in a mammal.

38. The method of claim 36, wherein said cell is a cell selected from the group consisting of a CNS cell and a lymphoid cell.

39. A method of combating a cancer in a mammal comprising administering to said mammal a pharmaceutical composition comprising a compound of claim 1 or a pharmaceutically acceptable salt thereof, in an amount effective to combat a cancer in the mammal.

40. The method of claim 39, wherein said cancer is a cancer selected from the group consisting of a carcinoma, a sarcoma, a neuroblastoma, a leukemia, a lymphoma and a solid tumor.

41. A kit for combating a cancer in a mammal, said kit comprising
a) a composition selected from the group consisting of a compound of claim 1, a pharmaceutically acceptable salt thereof, and a pharmaceutical composition comprising a compound of claim 1, and
b) an instructional material.

42. A kit for facilitating delivery of an anticancer agent to a mammalian cell, said kit comprising
a) a composition selected from the group consisting of a compound of claim 1, a pharmaceutically acceptable salt thereof, and a pharmaceutical composition comprising a compound of claim 1, and
b) an instructional material.

43. The compound of claim 1,
wherein,
$R^{11}$ is a $C_{12}$ alkyl, branched alkyl, alkenyl or alkynyl;
$R^{12}$ is $C_8H_{16}$ alkyl or branched alkyl;
n=1,
and $R^{13}$ is an anticancer agent selected from the group consisting of gemcitabine, 5-azacytidine, cladribine, fludarabine, fluorodeoxyuridine, cytosine arabinoside, 6-mercaptopurine, 6-thioguanine, 5-deoxyfluorouridine, ftorafur, capecitabine, 5-deoxy-5-fluorocytidine, 5-aza-cystine arabinoside, troxacitabine, and pentostatin, wherein the phosphorus atom of the phosphate moiety is covalently linked in a phosphate ester linkage to the oxygen atom of the 5' hydroxyl group of a sugar moiety of $R^{13}$.

44. The compound of claim 3,
wherein,
$R^{21}$ is $C_{12}$ alkyl;
$R^{22}$ is $C_{10}$ alkyl;
n=1, and
$R^{23}$ is an anticancer agent selected from the group consisting of gemcitabine, 5-azacytidine, cladribine, fludarabine, fluorodeoxyuridine, cytosine arabinoside, 6-mercaptopurine, 6-thioguanine, 5-deoxyfluorouridine, ftorafur, capecitabine, 5-deoxy-5-fluorocytidine, 5-aza-cytsine arabinoside, troxacitabine, and pentostatin, wherein the methylene group of the phosphonate moiety is covalently linked to the oxygen atom of the 5' hydroxyl group of a sugar moiety of $R^{23}$.

45. The compound of claim 5,
wherein,
$R^{31}$ is $(C_6-C_{16})$ alkyl, branched alkyl, alkenyl or alkynyl;
$R^{32}$ is $(C_1-C_8)$ alkyl, branched alkyl, alkenyl or alkynyl, and
$R^{33}$ an anticancer agent selected from the group consisting of mitoxanthrone, doxorubicin, idarubicin, epirubicin, daunorubicin, mitomycin, methotrexate, CPT-11, SN-38, camptothecin, topotecan, 9-nitrocamptothecin, and 9-aminocamptothecin, and is covalently linked via an ester, amido or carbamate linkage to the O, S or amino group of $X^{33}$.

* * * * *